United States Patent
Ferrone et al.

(10) Patent No.: US 10,881,711 B2
(45) Date of Patent: Jan. 5, 2021

(54) ANTI-CSPG4 REAGENTS AND METHODS OF TREATING CANCER

(71) Applicant: THE GENERAL HOSPITAL CORPORATION, Boston, MA (US)

(72) Inventors: Soldano Ferrone, Boston, MA (US); Xinhui Wang, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 159 days.

(21) Appl. No.: 15/564,580

(22) PCT Filed: Apr. 6, 2016

(86) PCT No.: PCT/US2016/026141
§ 371 (c)(1),
(2) Date: Oct. 5, 2017

(87) PCT Pub. No.: WO2016/164408
PCT Pub. Date: Oct. 13, 2016

(65) Prior Publication Data
US 2018/0072811 A1    Mar. 15, 2018

Related U.S. Application Data

(60) Provisional application No. 62/143,456, filed on Apr. 6, 2015.

(51) Int. Cl.
| | |
|---|---|
| *C07K 16/00* | (2006.01) |
| *A61K 39/395* | (2006.01) |
| *A61K 38/17* | (2006.01) |
| *C07K 14/47* | (2006.01) |
| *A61K 45/06* | (2006.01) |
| *C07K 16/30* | (2006.01) |
| *G01N 33/574* | (2006.01) |
| *A61P 35/00* | (2006.01) |
| *A61K 38/00* | (2006.01) |

(52) U.S. Cl.
CPC .... *A61K 38/1709* (2013.01); *A61K 39/39558* (2013.01); *A61K 45/06* (2013.01); *A61P 35/00* (2018.01); *C07K 14/47* (2013.01); *C07K 16/3053* (2013.01); *G01N 33/5743* (2013.01); *A61K 38/00* (2013.01); *C07K 2317/21* (2013.01); *C07K 2317/565* (2013.01); *C07K 2317/622* (2013.01); *C07K 2317/73* (2013.01); *G01N 2333/4722* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 2010/0172917 A1 | 7/2010 | Ter et al. | |
| 2013/0259865 A1 | 10/2013 | Wang et al. | |
| 2013/0259873 A1 | 10/2013 | Ferrone et al. | |
| 2014/0004124 A1 | 1/2014 | Ferrone et al. | |

FOREIGN PATENT DOCUMENTS

| | | |
|---|---|---|
| WO | 2014/165644 A2 | 10/2014 |
| WO | 2014/194100 A1 | 12/2014 |

OTHER PUBLICATIONS

Paul, Fundamental Immunology, 3rd Edition, 1993, pp. 292-295.*
Rudikoff et al, Proc. Natl. Acad. Sci. USA, 79(6):1979-1983, Mar. 1982.*
Colman P. M., Research in Immunology, 145:33-36, 1994.*
MacCallunn et al, J. Mol. Biol., 262, 732-745, 1996.*
Pascalis et al, Journal of Immunology, 2002, vol. 169, pp. 3076-3084.*
Casset et al, Biochemical and Biophysical Research Communications, 2003, vol. 307, pp. 198-205.*
Zigler et al, Curr Opinion Pharmacol, 13:504-510, 2013.*
Campoli et al., "Human high molecular weight-melanoma-associated antigen (HMW-MAA): a melanoma cell surface chondroitin sulfate proteoglycan (MSCP) with biological and clinical significance." Critical Reviews in Immunology 24(4):267-296 (2004).
Hong et al., "Isolation and characterization of CD34+ blast-derived exosomes in acute myeloid leukemia." PloS one 9(8):e103310 (2014).
Khan et al., "Plasma-derived exosomal survivin, a plausible biomarker for early detection of prostate cancer." PloS one 7(10):e46737 (2012).
Logozzi et al., "High levels of exosomes expressing CD63 and caveolin-1 in plasma of melanoma patients." PloS One 4(4):e5219 (2009).
Schlingemann et al., "Expression of the high molecular weight melanoma-associated antigen by pericytes during angiogenesis in tumors and in healing wounds." The American Journal of Pathology 136(6):1393-1405 (1990).

(Continued)

*Primary Examiner* — Mark Halvorson
(74) *Attorney, Agent, or Firm* — Nixon Peabody LLP; David S. Resnick; Nicole D. Kling

(57) ABSTRACT

Embodiments of the present invention provide antibodies, antigen binding portions thereof, and other polypeptides (e.g., CARs), that specifically bind to CSPG4, an antigen expressed on cancer cells. Monoclonal antibodies, antibody-drug conjugates, and/or CAR-T-cells that specifically bind to CSPG4 positive cancer cells are also provided.

15 Claims, 13 Drawing Sheets
Specification includes a Sequence Listing.

(56) References Cited

OTHER PUBLICATIONS

Temponi et al., "Binding parameters and idiotypic profile of the whole immunoglobulin and Fab'fragments of murine monoclonal antibody to distinct determinants of the human high molecular weight-melanoma associated antigen." Cancer Research 52(9):2497-2503 (1992).
Wang et al., "Detection of chondroitin sulfate proteoglycan 4 (CSPG4) in melanoma." Molecular Diagnostics for Melanoma 1102:523-535 (2014).
Wang et al., "Functional characterization of an scFv-Fc antibody that immunotherapeutically targets the common cancer cell surface proteoglycan CSPG4." Cancer Research 71(24):7410-7422 (2011).
Whiteside "Immune modulation of T-cell and NK (natural killer) cell activities by TEXs (tumour-derived exosomes)." Biochem Soc Trans. 41(1):245-251 (2013).

\* cited by examiner

TTCCGGCTCGTATGTTGTGTGGAATTGTGAGCGGATAACAATTTC
ACACAGGAAACAGCTATGACCATGATTACGCCAAGCTTGCATGCA
AATTCTATTTCAAGGAGACAGTCATAATGAAATACCTATTGCCTAC
GGCAGCCGCTGGATTGTTATTACTCGCGGCCCAGCCGG((*CCATG*
*GCCGAGGTGCAGCTGGTGGAGTCTGGGGGAGGTGTGGTACGGC*
*CTGGGGGGTCCCTGAGACTCTCCTGTGCAGCCTCTGGATTCACCT*
*TGATGATTATGGCATGAGCTGGGTCCGCCAAGCTCCAGGGAAG*
*GGGCTGGAGTGGGTCTCTGGTATTAATTGGAATGGTGGTAGCAC*
*AGGTTATGCAGACTCTGTGAAGGGCCGATTCACCATCTCCAGAGA*
*CAACGCCAAGAACTCCCTGTATCTGCAAATGAACAGTCTGAGAGC*
*CGAGGACACGGCCGTGTATTACTGTGCAAGGGGCGTGCTGTCGC*
*GTTATTTTGACTACTGGGGCCAAGGTACCCTGGTCACCGTCTCGA*
*GT[[GGTGGAGGCGGTTCAGGCGGAGGTGGCTCTGGCGGTGGC*
*GGATCG]]*GAAATTGAGCTCACACAGTCTCCAGCCACCCTGTCTTT
GTCTCCAGGGGAAAGAGCCACCCTCTCCTGCAGGGCCAGTCAGA
GTGTTAGCAGCTACTTAGCCTGGTACCAACAGAAACCTGGCCAG
GCTCCCAGGCTCCTCATCTATGATGCATCCAACAGGGCCACTGGC
ATCCCAGCCAGGTTCAGTGGCAGTGGGTCTGGGACAGACTTCAC
TCTCACCATCAGCAGCCTAGAGCCTGAAGATTTTGCAGTTTATTAC
TGTCAGCAGCGTAGCAACTGGCCTCCGGCTTTCGGCGGAGGGAC
CAAGGTGGAGATCAAACGTGCGGCCGC))AGAACAAAAACTCAT
CTCAGAAGAGGATCTGAATGGGGCCGCAT

*FIG. 3*

MetAEVQLVESGGGGVVRPGGSLRLSCAASGFTFDDY
G MetSWVRQAPGKGLEWVSGINWNGGSTGYADSV
KGRFTISRDNAKNSLYLQMetNSLRAEDTAVYYCARG
VLSRYFDYWGQGTLVTVSSGGGGSGGGGSGGGGS
EIELTQSPATLSLSPGERATLSCRASQSVSSYLAWYQ
QKPGQAPRLLIYDASNRATGIPARFSGSGSGTDFTL
TISSLEPEDFAVYYCQQRSNWPPAFGGGTKVEIKRA
A

```
                                    <------------------------------------------ FR1 - IMGT
                          1               5              10              15
                          E  V  Q  L  V  E  S  G  G      G  V  R  P
SK5_VH                    gag gtg cag ctg gtg gag tct ggg gga .... ggt gtg cgg cct
M99657 Homsap IGHV3-20*01 F  --- --- --- --- --- --- --- --- --- .... --- --- --- ---

------->
                                          20              25              30
                          G  G  S  L  R  L  S  C  A  A  S  G  F  T  F
SK5_VH                    ggg ggg tcc ctg aga ctc tcc tgt gca gcc tct gga ttc acc ttt
M99657 Homsap IGHV3-20*01 F  --- --- --- --- --- --- --- --- --- --- --- --- --- --- ---

_____ CDR1 - IMGT _____
                                         35              40              45
                                   D  D  Y  G  M  S  W  V  R  Q  A
SK5_VH                    .... ... gat gat tat ggc atg agc tgg gtc cgc caa gct
M99657 Homsap IGHV3-20*01 F  .... ... --- --- --- --- --- --- --- --- --- --- ---
```

FIG. 5 (con't.)

```
                    FR2 - IMGT  ------------------------------------>               CDR2
                                 50             55             60
                      P   G   K   G   L   E   W   V   S   G   I   N   W   N
SK5_VH              cca ggg aag ggg ctg gag tgg gtc tct ggt att aat tgg aat ...

M99657 Homsap IGHV3-20*01 F  --- --- --- --- --- --- --- --- --- --- --- --- --- --- ...

- IMGT                  <----------
                                 65             70             75
                      G   G   S   T   G   Y   A   D   S   V   K   G   R
SK5_VH              ... ggt ggt agc aca ggt tat gca gac tct gtg aag ... ggc cga M99657 Homsap IGHV3-20*01 F  ... --- --- --- --- --- --- --- --- --- --- ... --- ---

FR3 - IMGT  --------------
                                 80             85             90
                      F   T   I   S   R   D   N   A   K   N   S   L   Y   L   Q
SK5_VH              ttc acc atc tcc aga gac aac gcc aag aac tcc ctg tat ctg caa M99657 Homsap IGHV3-20*01 F  --- --- --- --- --- --- --- --- --- --- --- --- --- --- ---
```

FIG. 5 (cont.)

```
                                                95                              100                        104
SK5_VH                           M   N   S   L   R   A   E   D   T   A   V   Y   Y   C   A
                                 atg aac agt ctg aga gcc gag gac acg gcc gtg tat tac tgt gca
M99657 Homsap IGHV3-20*01 F                                         L       H
                                 --- --- --- --- --- --- --- --- --- --- --- t-- --- c-- ---g

|————————————— CDR3 - IMGT —————————————|

SK5_VH                           R   G   V   L   S   R   Y   F   D   Y   W   G   Q   G   T
                                 agg ggc gtg ctg tcg cgt tat ttt gac tac tgg ggc caa ggt acc
M99657 Homsap IGHV3-20*01 F      --a --a SK5_VH                           L   V   T   V   S   S
                                 ctg gtc acc gtc tcg agt
M99657 Homsap IGHV3-20*01 F
```

FIG. 6

```
FR1-IMGT          CDR1-IMGT    FR2-IMGT
                  CD
                  (1-26)              (27-38)              (39-55)
             1         10         20         30         40         50
             |.........|.........|.........|.........|.........|....
SK5_VH                       ........................            ..............
M99657 Homsap IGHV3-20*01 F  EVQLVESGG.GVVRPGGSLRLSCAAS GFTF....DDYG MSWVRQAPGKGLEWVSG IN
                             EVQLVESGG.GVVRPGGSLRLSCAAS GFTF....DDYG MSWVRQAPGKGLEWVSG IN R2-IMGT                      FR3-IMGT
                  56-65)                       (66-104)
             60         70         80         90         100
             |.........|.........|.........|.........|....
SK5_VH       ..........................................  V Y
M99657 Homsap IGHV3-20*01 F  WN..GGST GYADSVK.GRFTISRDNAKNSLYLQMNSLRAEDTAVYYC A
                             WN..GGST GYADSVK.GRFTISRDNAKNSLYLQMNSLRAEDTALYHC AR
```

FIG. 7

```
                              <-------------------------------------------- FR1 - IMGT
                              1               5                  10                 15
                              E   I   E   L   T   Q   S   P   A   T   L   S   L   S   P
SK5_VL                        gaa att gag ctc aca cag tct cca gcc acc ctg tct ttg tct cca
                                              V
X01668 Homsap IGKV3-11*01 F   --- --- --- --- --- --- --- --- --- --- --- --- --- --- ---
                                              -t- t-g -------->
                                      20                 25                 30
                              G   E   R   A   T   L   S   C   R   A   S   Q   S   V
SK5_VL                        ggg gaa aga gcc acc ctc tcc tgc agg gcc agt cag agt gtt ...
X01668 Homsap IGKV3-11*01 F   --- --- --- --- --- --- --- --- --- --- --- --- --- --- ...

____ CDR1 - IMGT _____<---
                                               35                 40                 45
                                      S   S   Y   L   A   W   Y   Q   Q   K
SK5_VL                        ... ... agc agc tac tta gcc tgg tac caa cag aaa
X01668 Homsap IGKV3-11*01 F   ... ... --- --- --- --- --- --- --- --- --- ---
```

FIG. 7 (con't.)

```
                              FR2 - IMGT  ------------------------------------>        CDR2
                                       50         55         60
                              P   G   Q   A   P   R   L   L   I   Y   D   A
SK5_VL                        cct ggc cag gct ccc agg ctc ctc atc tat gat gca   ...   ...

X01668 Homsap IGKV3-11*01 F   --- --- --- --- --- --- --- --- --- --- --- ---   ...   ...

<---------- IMGT
                                       65         70         75
                              S   N   R   A   T   G   I   P   A   R
SK5_VL                    ... ... tcc aac agg gcc act ggc atc cca ... gcc agg X01668 Homsap IGKV3-11*01 F ... ... --- --- --- --- --- --- --- ---     --- ---

FR3 - IMGT  -----------------
                                       80         85         90
                              F   S   G   S   G   S   G   T   D   F   T   L   T
SK5_VL                        ttc agt ggc agt ggg ... ... tct ggg aca gac ttc act ctc acc X01668 Homsap IGKV3-11*01 F   --- --- --- --- ---         --- --- --- --- --- --- --- ---
```

FIG. 7 (con't.)

```
                                          95                    100                 104
                                I  S  S  L  E  P  E  D  F  A  V  Y  Y  C  Q
SK5_VL                          atc agc agc cta gag cct gaa gat ttt gca gtt tat tac tgt cag
X01668 Homsap IGKV3-11*01 F     --- --- --- --- --- --- --- --- --- --- --- --- --- --- ---

CDR3 - IMGT
                                Q  R  S  N  W  P  P  A  F  G  G  G  T  K  V
SK5_VL                          cag cgt agc aac tgg cct ccg gct ttc ggc gga ggg acc aag gtg
X01668 Homsap IGKV3-11*01 F     --- --- --- --- --- --- --- ---

E  I  K  R  A  A
SK5_VL                          gag atc aaa cgt gcg gcc gc
X01668 Homsap IGKV3-11*01 F
```

ANTI-CSPG4 REAGENTS AND METHODS OF TREATING CANCER

CROSS-REFERENCE TO RELATED APPLICATIONS

This application is a 35 U.S.C. § 371 National Phase Entry Application of International Application No. PCT/US2016/026141 filed Apr. 6, 2016, which designates the U.S. and claims benefit under 35 U.S.C. § 119(e) of U.S. Provisional Application No. 62/143,456 filed Apr. 6, 2015, the contents of which are incorporated herein by reference in their entireties.

GOVERNMENT SUPPORT

This invention was made with federal funding under Grant Nos. CA138188 awarded by the National Institutes of Health. The U.S. government has certain rights in the invention.

SEQUENCE LISTING

The instant application contains a Sequence Listing which has been submitted electronically in ASCII format and is hereby incorporated by reference in its entirety. Said ASCII copy, created on Apr. 5, 2016, is named 030258-083851-PCT_SL.txt and is 30,205 bytes in size.

BACKGROUND

Chondroitin sulfate proteoglycan (CSPG4) is a cell surface proteoglycan expressed on a variety of cancer cells, e.g., melanoma, triple negative breast cancer, glioma, head and neck squamous cell carcinoma, mesothelioma, chordoma and chondrosarcoma lesions, and on 11q23 positive acute leukemic samples. Significantly, CSPG4 expression has also been detected on cancer stem cells. Moreover, CSPG4 promotes signaling pathways for tumor cell proliferation, survival and migration. In contrast, CSPG4 has a restricted distribution in normal tissues. Its distinguished expression on cancer cells vs. normal tissues makes CSPG4 a potential target for antibody- or T cell-based targeted therapies.

SUMMARY

Described herein are antibodies, antigen binding portions thereof, and other polypeptides (e.g., CARs), that specifically bind to CSPG4. Such reagents can permit targeted therapies, e.g., monoclonal antibodies, antibody-drug conjugates, and/or CAR-T-cells that selectively target cancer cells.

In one aspect, described herein is an isolated antibody, antigen-binding portion thereof, or chimeric antigen receptor (CAR), the antibody, antigen-binding portion thereof, or CAR comprising any one of the heavy and light chain complimentarity determining regions (CDRs) selected from the group consisting of:
  a. a light chain CDR1 having the amino acid sequence of SEQ ID NO: 4;
  b. a light chain CDR2 having the amino acid sequence of SEQ ID NO: 5;
  c. a light chain CDR3 having the amino acid sequence of SEQ ID NO: 6;
  d. a heavy chain CDR1 having the amino acid sequence of SEQ ID NO: 1;
  e. a heavy chain CDR2 having the amino acid sequence of SEQ ID NO: 2; and
  f. a heavy chain CDR3 having the amino acid sequence of SEQ ID NO: 3.

In some embodiments, the isolated antibody, antigen-binding portion thereof, or CAR can comprise the light chain complimentarity determining regions (CDRs):
  a. a light chain CDR1 having the amino acid sequence of SEQ ID NO: 4;
  b. a light chain CDR2 having the amino acid sequence of SEQ ID NO: 5; and
  c. a light chain CDR3 having the amino acid sequence of SEQ ID NO: 6.

In some embodiments, the isolated antibody, antigen-binding portion thereof, or CAR can comprise the heavy chain complimentarity determining regions (CDRs):
  a. a heavy chain CDR1 having the amino acid sequence of SEQ ID NO: 1;
  b. a heavy chain CDR2 having the amino acid sequence of SEQ ID NO: 2; and
  c. a heavy chain CDR3 having the amino acid sequence of SEQ ID NO: 3.

In some embodiments, the isolated antibody, antigen-binding portion thereof, or CAR can comprise the complimentarity determining regions (CDRs):
  a. a light chain CDR1 having the amino acid sequence of SEQ ID NO: 4;
  b. a light chain CDR2 having the amino acid sequence of SEQ ID NO: 5;
  c. a light chain CDR3 having the amino acid sequence of SEQ ID NO: 6;
  d. a heavy chain CDR1 having the amino acid sequence of SEQ ID NO: 1;
  e. a heavy chain CDR2 having the amino acid sequence of SEQ ID NO: 2; and
  f. a heavy chain CDR3 having the amino acid sequence of SEQ ID NO: 3.

In some embodiments, the isolated antibody, antigen-binding portion thereof, or CAR can comprise the sequence of SEQ ID NO: 7. In some embodiments, the isolated antibody, antigen-binding portion thereof, or CAR can comprise the sequence of SEQ ID NO: 24. In some embodiments, the isolated antibody, antigen-binding portion thereof, or CAR can comprise the sequence of SEQ ID NO: 25.

In some embodiments, the isolated antibody, antigen-binding portion thereof, or CAR can comprise a conservative substitution in a sequence not comprised by a CDR. In some embodiments, the antibody or polypeptide is selected from the group consisting of: an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody. In some embodiments, the isolated antibody, antigen-binding portion thereof, or CAR is fully human. In some embodiments, the isolated antibody, antigen-binding portion thereof, or CAR has fully human antigen-binding domains. In some embodiments, the isolated antibody, antigen-binding portion thereof, or CAR specifically binds to CSPG4.

In one aspect, described herein is a nucleic acid encoding an isolated antibody, antigen-binding portion thereof, or CAR as described herein. In some embodiments, one or more of the nucleic acid sequences comprises a sequence selected from SEQ ID NOs: 8-11. In some embodiments, the nucleic acid is a cDNA.

In one aspect, described herein is a cell comprising the isolated antibody, antigen-binding portion thereof, or CAR as described herein. In some embodiments, the cell is an immune cell. In some embodiments, the cell is selected from the group consisting of: a T cell; a NK cell; and a NKT cell. In some embodiments, the isolated antibody, antigen-binding portion thereof, or CAR is expressed on the cell surface.

In one aspect, described herein is a composition comprising the isolated antibody or antigen-binding portion thereof as described herein, and a chemotherapeutic agent. In some embodiments, the antibody or antigen-binding portion thereof is conjugated to the chemotherapeutic agent.

In one aspect, described herein is a pharmaceutical composition comprising an isolated antibody, antigen-binding portion thereof, or CAR, the nucleic acid, the cell, or the composition as described herein, and a pharmaceutically acceptable carrier.

In one aspect, described herein is a method of inhibiting or killing a CSPG4+ cell, the method comprising contacting the cell with an isolated antibody, antigen-binding portion thereof, or CAR, the nucleic acid, the cell, or the composition as described herein.

In one aspect, described herein is a method of treating cancer in a subject in need thereof, the method comprising administering a therapeutically effective amount of an isolated antibody, antigen-binding portion thereof, or CAR, the nucleic acid, the cell, or the composition as described herein. In one aspect, described herein is a method of treating cancer in a subject in need thereof, the method comprising administering a cell as described herein to the subject. In one aspect, described herein is a method of treating cancer in a subject in need thereof, the method comprising administering a nucleic acid as described herein to the subject, wherein the subject's T-cells are caused to express the polypeptide encoded by the nucleic acid. In some embodiments, the cancer is selected from the group consisting of: melanoma; breast cancer; triple negative breast cancer; glioma; head and neck cancer; head and neck squamous cell carcinoma; carcinoma; mesothelioma; chordoma; condrosarcoma; sarcoma; leukemia; 11q23 positive acute leukemia; acute leukemia; and a CSPG4+ cancer or tumor.

In one aspect, described herein is an assay comprising: contacting a test sample obtained from the subject with an antibody or antigen-binding portion thereof as described herein; and detecting the presence or intensity of a signal which indicates the presence or level of CSPG4 in the sample; wherein an increase in the CSPG4 level relative to a reference level indicates the subject has a higher risk of having or developing cancer. In some embodiments, an increase in the CSPG4 level relative to a reference level indicates the subject has a higher risk of having or developing CSPG4+ cancer. In some embodiments, the increase in the CSPG4 level relative to a reference level indicates the subject has CSPG4+ cancer.

In one aspect, described herein is a method of identifying a subject in need of treatment for cancer, the method comprising: contacting a test sample obtained from the subject with an antibody or antigen-binding portion thereof as described herein; detecting the presence or intensity of a signal which indicates the presence or level of CSPG4 in the sample; identifying the subject as being in need of treatment for cancer when the expression level of CSPG4 is increased relative to a reference level. In one aspect, described herein is a method of determining if a subject is at risk for cancer, the method comprising: contacting a test sample obtained from the subject with an antibody or antigen-binding portion thereof as described herein; detecting the presence or intensity of a signal which indicates the presence or level of CSPG4 in the sample; comparing the level of CSPG4 in the sample to a reference level of CSPG4; determining that the subject is at risk for cancer when the level of CSPG4 is increased relative to a reference level; and determining that the subject is not at risk for cancer when the level of CSPG4 is not increased relative to a reference level. In one aspect, described herein is a method of determining if a subject is likely to respond to treatment with anti-CSPG4 therapy, contacting a test sample obtained from the subject with an antibody or antigen-binding portion thereof as described herein; detecting the presence or intensity of a signal which indicates the presence or level of CSPG4 in the sample; determining that the subject is likely to respond to treatment with anti-CSPG4 therapy when the level of CSPG4 is increased relative to a reference level; and determining that the subject is not likely to respond to treatment with anti-CSPG4 when the level of CSPG4 is not increased relative to a reference level. In one aspect, described herein is a method of determining the efficacy of a treatment for cancer, the method comprising: (a) contacting a test sample obtained from the subject with an antibody or antigen-binding portion thereof as described herein and detecting the presence or intensity of a signal which indicates the presence or level of CSPG4 in the sample before administration of the treatment; (b) contacting a test sample obtained from the subject with an antibody or antigen-binding portion thereof as described herein and detecting the presence or intensity of a signal which indicates the presence or level of CSPG4 in the sample after administration of the treatment; (c) determining that the treatment is efficacious when the level determined in step (b) is decreased relative to the expression level determined in step (a); and (d) determining that the treatment is not efficacious when the expression level determined in step (b) is increased relative to the expression level determined in step (a). In one aspect, described herein is a method of treatment for cancer, the method comprising; contacting a test sample obtained from the subject with an antibody or antigen-binding portion thereof as described herein; detecting the presence or intensity of a signal which indicates the presence or level of CSPG4 in the sample; treating the subject with an anti-CSPG4 therapy when the level of CSPG4 is increased relative to a reference level. In one aspect, described herein is a method of treating cancer, the method comprising; administering a therapeutically effective amount of an anti-CSPG4 therapy to a subject determined to be in need of treatment for cancer and further determined to have a level of CSPG4 that is increased relative to a reference level. In one aspect, described herein is a method of detecting CSPG4, the method comprising contacting a biological sample with an antibody or antigen-binding portion thereof as described herein, wherein reaction of the antibody or antigen-binding portion thereof with CSPG4 indicates the presence of CSPG4.

In some embodiments, a detectable signal is generated by the antibody or antigen-binding portion thereof when a CSPG4 molecule is present. In some embodiments, the antibody or antigen-binding portion thereof is detectably labeled or capable of generating a detectable signal. In some embodiments, the level of the CSPG4 is determined using a method selected from the group consisting of: Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay. In some embodiments, the antibody or antigen-binding portion thereof is detectably labeled or generates a detectable signal. In some embodiments, the expression level of CSPG4 is normalized relative to the expression level of one or more reference genes or reference proteins. In some embodiments, the reference level of CSPG4 is the expression level of CSPG4 in a prior sample obtained from the subject. In some embodiments, the assay or method can further comprise the step of administering an anti-CSPG4 therapy. In some embodiments, the anti-CSPG4 therapy comprises an isolated antibody, antigen-binding portion thereof, or, the nucleic acid, the cell, or the composition as described herein.

In some embodiments, the level of CSPG4 is the level of CSPG4 comprised by exosomes. In some embodiments, the assay or method can further comprise a step of isolating exosomes from the sample.

In one aspect, described herein is a kit for performing the method or assay as described herein, comprising an isolated antibody, or antigen-binding portion thereof as described herein.

In one aspect, described herein is a chimeric antigen receptor (CAR) comprising: an extracellular domain that comprises an anti-CSPG4 antibody or antigen binding portion thereof that binds one or more epitopes of a human CSPG4 polypeptide; a transmembrane domain, one or more intracellular co-stimulatory signaling domains, and a primary signaling domain. In some embodiments, the anti-CSPG4 antibody or antigen binding portion that binds the human CSPG4 polypeptide is selected from the group consisting of: a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody). In some embodiments, the anti-CSPG4 antibody or antigen binding portion thereof comprises one or more CDRs as set forth in any one of SEQ ID NOs: 1-6. In some embodiments, the transmembrane domain is from a polypeptide selected from the group consisting of: alpha, beta or zeta chain of the T-cell receptor, CD3ε, CD3ζ, CD4, CD5, CD8α, CD9, CD 16, CD22, CD27, CD28, CD33, CD37, CD45, CD64, CD80, CD86, CD 134, CD137, CD152, CD 154, and PD1. In some embodiments, the one or more co-stimulatory signaling domains are from a co-stimulatory molecule selected from the group consisting of: CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70. In some embodiments, the primary signaling domain is CD3ζ. In one aspect, described herein is a polynucleotide encoding a CAR as described herein. In one aspect, described herein is a vector comprising a polynucleotide encoding a CAR as described herein. In some embodiments, the vector is a retroviral vector. In some embodiments, the vector is a lentiviral vector. In some embodiments, the lentiviral vector is selected from the group consisting essentially of: human immunodeficiency virus 1 (HIV-1); human immunodeficiency virus 2 (HIV-2), visna-maedi virus (VMV) virus; caprine arthritis-encephalitis virus (CAEV); equine infectious anemia virus (EIAV); feline immunodeficiency virus (FIV); bovine immune deficiency virus (BIV); and simian immunodeficiency virus (SIV). In one aspect, described herein is an immune cell comprising the vector of the foregoing aspects. In some embodiments, the immune cell is selected from the group consisting of: a T lymphocyte and a natural killer (NK) cell.

In one aspect, described herein is a composition comprising the immune cell of the foregoing aspects and a physiologically acceptable excipient.

In one aspect, described herein is a method of treating a cancer in a subject in need thereof, comprising administering to the subject a therapeutically effective amount of the composition of the foregoing aspects. In some embodiments, the cancer is selected from the group consisting of: melanoma; breast cancer; triple negative breast cancer; glioma; head and neck cancer; head and neck squamous cell carcinoma; carcinoma; mesothelioma; chordoma; condrosarcoma; sarcoma; leukemia; 11q23 positive acute leukemia; acute leukemia; and a CSPG4+ cancer or tumor.

In one aspect, described herein is an assay comprising contacting a sample comprising exosomes obtained from a subject with an antibody or antigen-binding portion thereof as described herein; and detecting the presence or intensity of a signal which indicates the presence or level of CSPG4 in the sample; wherein an increase in the CSPG4 level relative to a reference level indicates the subject has a higher risk of having or developing cancer. In some embodiments, the assay can further comprise a step of isolating the exosomes. In some embodiments, the step of isolating the exosomes is performed prior to contacting the sample with the antibody or antigen-binding portion thereof. In some embodiments, an increase in the CSPG4 level relative to a reference level indicates the subject has a higher risk of having or developing CSPG4+ cancer. In some embodiments, the increase in the CSPG4 level relative to a reference level indicates the subject has CSPG4+ cancer.

In one aspect, described herein is a method of isolating exosomes originating from CSPG4+ cells, the method comprising contacting a sample comprising exosomes with an antibody or antigen-binding portion thereof of as described herein; and isolating exosomes bound to an antibody or antigen-binding portion thereof. In some embodiments, the antibody or antigen-binding portion thereof can be detectably labeled and/or epitope-tagged. In some embodiments, the antibody or antigen-binding portion thereof is conjugated to a solid support.

BRIEF DESCRIPTION OF THE DRAWINGS

FIG. 3 depicts scFv SK5 nucleic acid sequence (SEQ ID NO: 8). The sequence in italics and between double parentheses is the scFv SK5 which is used for translation and IMTG analysis as described herein (flanked by NcoI and NotI restriction sites). The first codon of the VH and the VL sequences are shown, respectively in bold. The linker sequence is shown between the double brackets. The XhoI site is bolded and underlined.

FIG. 4 depicts scFv SK5 amino acid sequence (SEQ ID NO: 7).

FIG. 5 depicts an alignment of scFv SK5 VH (IMGT numbering scheme) SK5_VH amino acid sequence (SEQ ID NO: 14); SK5_VH nucleic acid sequence (SEQ ID NO: 15); M99657 Homsap IGHV3-20*01 F amino acid sequence (SEQ ID NO: 40); M99657 Homsap IGHV3-20*01 F nucleic acid sequence (SEQ ID NO: 39).

FIG. 6 depict an alignment of V-region protein display with positions of CDRs (SEQ ID NOS 41-42, respectively, in order of appearance)

FIG. 7 depicts an alignment of scFv SK5 VL (IMGT numbering scheme) SK5_VL amino acid sequence (SEQ ID NO: 16); SK5_VL nucleic acid sequence (SEQ ID NO: 17); X01668 Homsap IGKV3-11*01 F amino acid sequence (SEQ ID NO: 44); X01668 Homsap IGKV3-11*01 F nucleic acid sequence (SEQ ID NO: 43).

DETAILED DESCRIPTION

Figure 1:
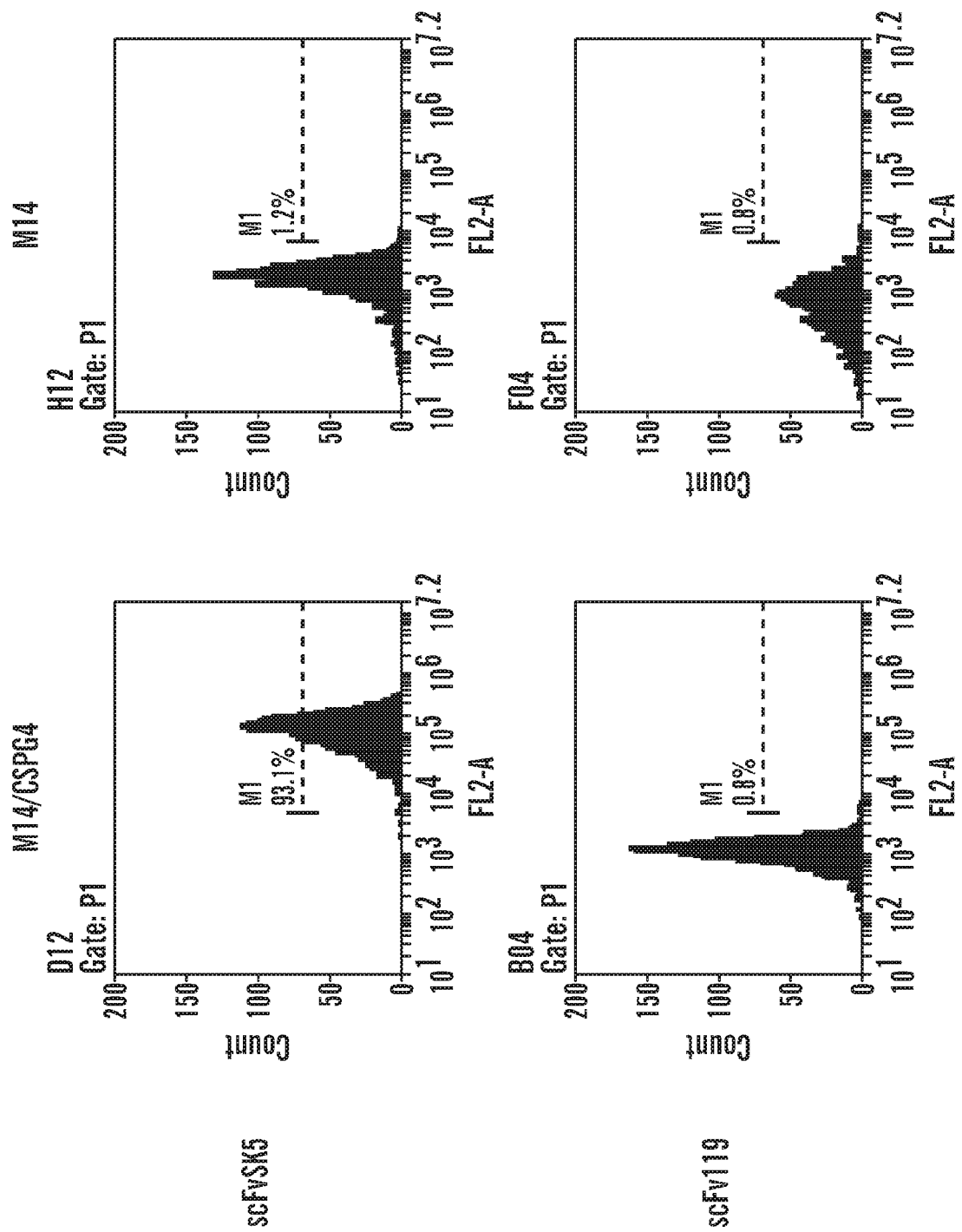
FIG. 1 demonstrates differential staining by scFv SK5 of CSPG4+ M14/CSPG4 melanoma cells and CSPG4− parental M14 melanoma cells. M14/CSPG4 transfectants and parental CSPG4− M14 cells were incubated on ice with supernatant (SNT) containing soluble scFv SK5 (with a c-Myc tag) and c-Myc-specific mAb 9E10 and control SNT scFv 119 and mAb 9E10, with CSPG4-specific mouse mAb 763.74 (0.5 µg) and isotype control mAb MK2-23 as a positive control and negative control. Binding of antibodies was detected using RPE-labeled F(ab')$_2$ fragments of goat anti-mouse Ig antibodies. Cells were analyzed with a FACScan flow cytometer.
Figure 1:
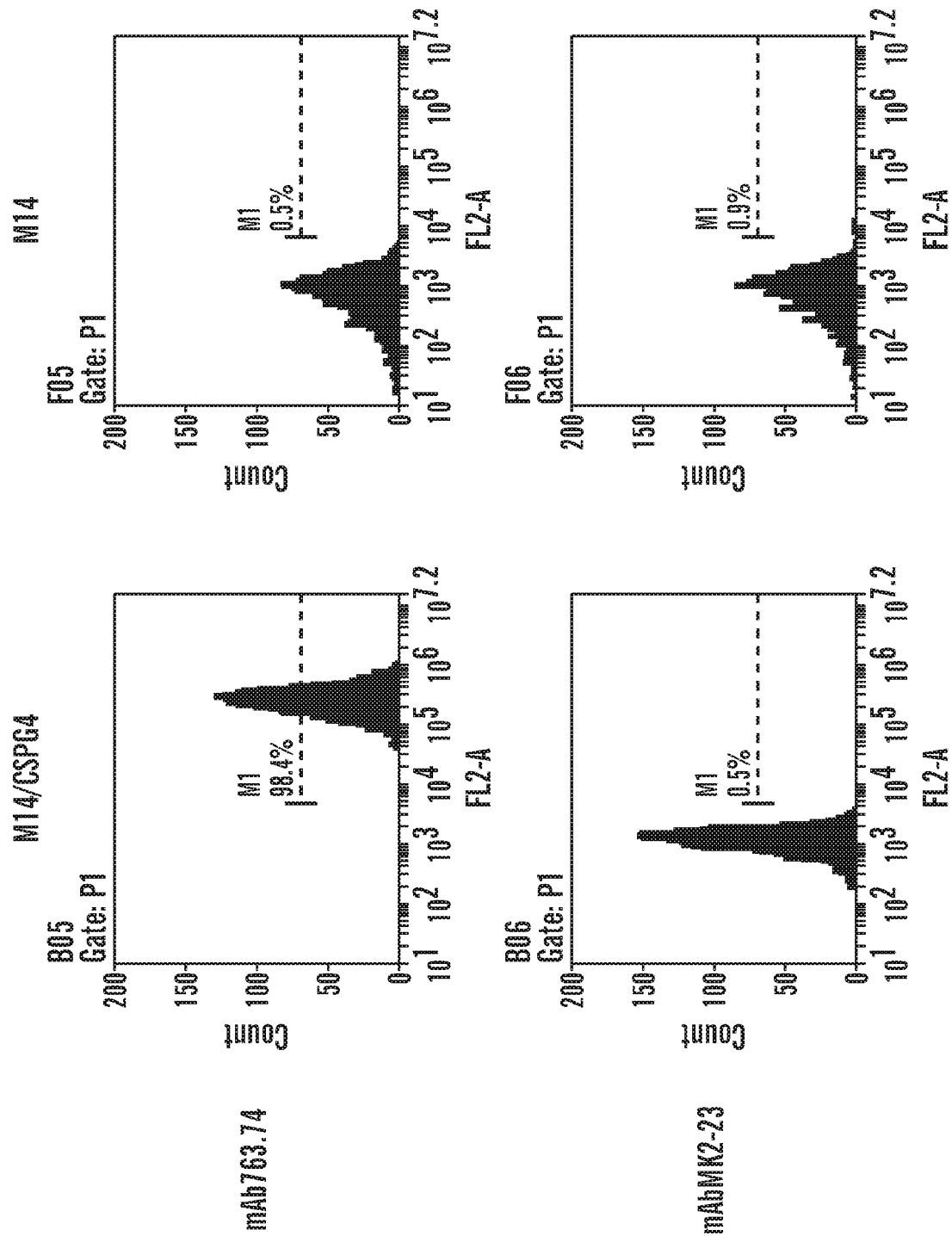

Described herein are antibodies, antigen binding portions thereof, and related polypeptides that bind specifically to CSPG4, e.g., CSPG4 expressed on the surface of cancer cells. Such antibodies, antigen binding portions thereof, and polypeptides can permit, e.g., the diagnosis, prognosis, and/or treatment of cancer. In some embodiments, the technology described herein relates to chimeric antigen receptors (CARs) and CAR-T therapy for cancer. In some embodiments, the technology described herein relates to monoclonal antibody therapy for cancer. In some embodiments, the technology described herein relates to antibody-drug conjugates for the treatment of cancer.

As used herein, "CSPG4" or "chondroitin sulfate proteoglycan 4" is also known as melanoma-associated chondroitin sulfate proteoglycan (MCSP), neuron-glial antigen 2 (NG2), and high molecular weight melanoma associated antigen (HMW-MAA). CSPG4 refers to a chondroitin sulfate proteoglycan that stabilizes cell-substratum interactions, e.g., during melanoma cell spreading. CSPGs comprise a protein core and chondroitin sulfate side chain and are known to interact with, e.g., ECM, laminin, fibronectin, tenascin, and/or collagen. The sequence of CSPG4 for a number of species is well known in the art, e.g., human CSPG4 (e.g., NCBI Gene ID: 1464; (mRNA: NCBI Ref Seq: NM_001897) (polypeptide: NCBI Ref Seq: NP_001888).

In one aspect, described herein is an isolated antibody, antigen-binding portion thereof, or chimeric antigen receptor (CAR) comprising one or more heavy and/or light chain complimentarity determining regions (CDRs) selected from the group consisting of:
  a. a light chain CDR1 having the amino acid sequence of SEQ ID NO: 4;
  b. a light chain CDR2 having the amino acid sequence of SEQ ID NO: 5;
  c. a light chain CDR3 having the amino acid sequence of SEQ ID NO: 6;
  d. a heavy chain CDR1 having the amino acid sequence of SEQ ID NO: 1;
  e. a heavy chain CDR2 having the amino acid sequence of SEQ ID NO: 2; and
  f. a heavy chain CDR3 having the amino acid sequence of SEQ ID NO: 3.

In some embodiments, the antibody, antigen-binding portion thereof, or chimeric antigen receptor (CAR) specifically binds to CSPG4.

In some embodiments, the isolated antibody, antigen-binding portion thereof, or CAR comprises the light chain complimentarity determining regions (CDRs):
  a. a light chain CDR1 having the amino acid sequence of SEQ ID NO: 4;
  b. a light chain CDR2 having the amino acid sequence of SEQ ID NO: 5; and
  c. a light chain CDR3 having the amino acid sequence of SEQ ID NO: 6.

In some embodiments, the isolated antibody, antigen-binding portion thereof, or CAR comprises the heavy chain complimentarity determining regions (CDRs):
  a. a heavy chain CDR1 having the amino acid sequence of SEQ ID NO: 1;
  b. a heavy chain CDR2 having the amino acid sequence of SEQ ID NO: 2; and
  c. a heavy chain CDR3 having the amino acid sequence of SEQ ID NO: 3.

In some embodiments, the isolated antibody, antigen-binding portion thereof, or CAR comprises the complimentarity determining regions (CDRs):
  a. a light chain CDR1 having the amino acid sequence of SEQ ID NO: 4;
  b. a light chain CDR2 having the amino acid sequence of SEQ ID NO: 5;
  c. a light chain CDR3 having the amino acid sequence of SEQ ID NO: 6;
  d. a heavy chain CDR1 having the amino acid sequence of SEQ ID NO: 1;
  e. a heavy chain CDR2 having the amino acid sequence of SEQ ID NO: 2; and
  f. a heavy chain CDR3 having the amino acid sequence of SEQ ID NO: 3.

In some embodiments, the isolated antibody, antigen-binding portion thereof, or CAR comprises the sequence of SEQ ID NO: 7. In some embodiments, the isolated antibody, antigen-binding portion thereof, or CAR comprises the sequence of SEQ ID NO: 24. In some embodiments, the isolated antibody, antigen-binding portion thereof, or CAR comprises the sequence of SEQ ID NO: 25. In some embodiments, the isolated antibody, antigen-binding portion thereof, or CAR as described herein, comprises a conservative substitution in a sequence not comprised by a CDR.

In some embodiments, the antibody, antigen-binding portion thereof, and/or CAR is an isolated polypeptide. In some embodiments, the antibody, antigen-binding portion thereof, and/or CAR is a purified polypeptide. In some embodiments, the antibody, antigen-binding portion thereof, and/or CAR is an engineered polypeptide.

In some embodiments, the isolated antibody, antigen-binding portion thereof is selected from the group consisting of: an immunoglobulin molecule, a monoclonal antibody, an antigen-binding portion of an antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody.

In some embodiments, a CAR comprises an extracellular domain comprising an anti-CSPG4 antibody or antigen-binding portion thereof that binds one or more epitopes of a CSPG4 polypeptide; a transmembrane domain, one or more intracellular co-stimulatory signaling domains, and a primary signaling domain.

In particular embodiments wherein an antibody, antigen-binding portion thereof, or CAR as described herein comprises at least one CDR which is not identical to the sequence of SEQ ID NOs: 1-6, the amino acid sequence of that at least one CDR can be selected by methods well known to one of skill in the art. For example, Fujii, 2004, "Antibody affinity maturation by random mutagenesis" in Methods in Molecular Biology: Antibody Engineering 248: 345-349 (incorporated by reference herein in its entirety), particularly at FIG. 2 and Section 3.3, describes methods of generating a library for any CDR of interest. This allows one of ordinary skill in the art to identify alternative CDRs, including conservative substitution variants of the specific CDR sequences described herein, which, when present in an antibody or antigen-binding portion thereof as described herein, will result in an antigen or antigen-binding portion thereof which will bind a cancer cell surface antigen. The method described in Fujii et al. also permits one of ordinary skill in the art to screen for a light chain sequence which will give the desired binding behavior when combined with a known heavy chain fragment and vice versa.

In some embodiments, the antibody or antigen-binding portion thereof described herein can be bispecific. Bispecific agents comprise a molecule which is able to physically contact and inhibit at least CSPG4 and another antigen simultaneously. As used herein, the term "bispecific agent" refers to a polypeptide that comprises a first polypeptide domain which has a binding site that has binding specificity for a first target, and a second polypeptide domain which has a binding site that has binding specificity for a second target, i.e., the agent has specificity for two targets, e.g., CSPG4 and a second antigen. The first target and the second target are not the same (i.e., are different targets (e.g., proteins)). In some embodiments, the different targets can be co-expressed on the same cell. In some embodiments, a bispecific polypeptide agent can bind targets present on a single cell (heterophilic binding in cis), and/or bind one target on one cell and the other on another cell (heterophilic binding in trans). Accordingly, a bispecific polypeptide agent as described herein can selectively and specifically bind to a cell that expresses the first target and the second target. Bispecific antibody reagents comprising antigen-binding portions of antibodies specific for two different antigens, e.g., CSPG4 and a second antigen, can be readily constructed by one of skill in the art. Generally, sequences encoding the antigen-binding domain of a first antibody characterized and known to bind a desired epitope on one antigen can be joined, either directly, or through any of a variety of linkers as known to the ordinarily skilled artisan, to sequences encoding the antigen-binding domain of a second antibody characterized and known to bind a desired epitope on a second antigen. Such sequences can be inserted into an appropriate vector and introduced to a cell to produce the bispecific antibody polypeptide by methods known to those of ordinary skill in the art. In some embodiments, the second antigen of a bispecific reagent can be a cancer cell marker, e.g., a molecule expressed more highly or exclusively on cancer cells as compared to normal cells of the same cell type.

In some embodiments, the bispecific antibody is a bispecific T cell engager (BiTE) that comprises a first antibody or antigen binding portion thereof that has binding specificity for an antigen on a target cell and a second antibody or antigen binding portion thereof that binds a T cell.

In some embodiments, the technology described herein relates to antibodies and/or polypeptides comprising an antigen-binding portion of an antibody, and/or a CAR which bind a cancer cell surface antigen. As used herein, "chimeric antigen receptor" or "CAR" refers to an artificially constructed hybrid polypeptide comprising an antigen-binding domain (e.g., an antigen-binding portion of an antibody (e.g., a scFV)), a transmembrane domain, and a T-cell signaling and/or T-cell activation domain. CARs have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains. Most commonly, the CAR's extracellular binding domain is composed of a single chain variable fragment (scFv) derived from fusing the variable heavy and light regions of a murine or humanized monoclonal antibody. Alternatively, scFvs may be used that are derived from Fab's (instead of from an antibody, e.g., obtained from Fab libraries), in various embodiments, this scFv is fused to a transmembrane domain and then to an intracellular signaling domain. "First-generation" CARs include those that solely provide CD3zeta (CD3ζ) signals upon antigen binding, "Second-generation" CARs include those that provide both costimulation (e.g., CD28 or CD 137) and activation (CD3ζ). "Third-generation" CARs include those that provide multiple costimulatory (e.g., CD28 and CD 137) domains and activation domains (e.g., CD3ζ). In various embodiments, the CAR is selected to have high affinity or avidity for the antigen. Further discussion of CARs can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

In various embodiments, a CAR comprises an extracellular binding domain that comprises a humanized CSPG4-specific binding domain; a transmembrane domain; one or more intracellular co-stimulatory signaling domains; and a primary signaling domain.

As used herein, the terms, "binding domain," "extracellular domain," "extracellular binding domain," "antigen-specific binding domain," and "extracellular antigen specific binding domain," are used interchangeably and provide a CAR with the ability to specifically bind to the target antigen of interest, e.g., CSPG4. The binding domain may be derived either from a natural, synthetic, semi-synthetic, or recombinant source.

In certain embodiments, the CARs contemplated herein may comprise linker residues between the various domains, e.g., added for appropriate spacing and conformation of the molecule. In particular embodiments the linker is a variable region linking sequence. A "variable region linking sequence," is an amino acid sequence that connects the VH and VL domains and provides a spacer function compatible with interaction of the two sub-binding domains so that the resulting polypeptide retains a specific binding affinity to the same target molecule as an antibody that comprises the same light and heavy chain variable regions. CARs contemplated herein, can comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

Illustrative examples of linkers include glycine polymers (G)n; glycine-serine polymers (G1-5S1-5)n, where n is an integer of at least one, two, three, four, or five (SEQ ID NO: 37); glycine-alanine polymers; alanine-serine polymers; and other flexible linkers known in the art. Glycine and glycine-serine polymers are relatively unstructured, and therefore may be able to serve as a neutral tether between domains of fusion proteins described herein. Glycine accesses significantly more phi-psi space than even alanine, and is much less restricted than residues with longer side chains (see Scheraga, Rev. Computational Chem. 11173-142 (1992)). The ordinarily skilled artisan will recognize that design of a composition as described herein in particular embodiments can include linkers that are all or partially flexible, such that the linker can include a flexible linker as well as one or more portions that confer less flexible structure to provide for a desired protein structure.

Other exemplary linkers include, but are not limited to the following amino acid sequences: GGG; DGGGS (SEQ ID NO: 26); TGEKP (SEQ ID NO: 27) (see, e.g., Liu et al., PNAS 5525-5530 (1997)); GGRR (SEQ ID NO: 28) (Pomerantz et al. 1995, supra); (GGGGS)n wherein=1, 2, 3, 4 or 5 (SEQ ID NO: 29) (Kim et al., PNAS 93, 1156-1160 (1996); EGKSSGSGSESKVD (SEQ ID NO: 30) (Chaudhary et al., 1990, Proc. Natl. Acad. Sci. U.S.A. 87:1066-1070); KESGSVSSEQLAQFRSLD (SEQ ID NO: 31) (Bird et al., 1988, Science 242:423-426), GGRRGGGS (SEQ ID NO: 32); LRQRDGERP (SEQ ID NO: 33); LRQKDGGGSERP (SEQ ID NO: 34); LRQKD(GGGS)2 ERP (SEQ ID NO: 35). Alternatively, flexible linkers can be rationally designed using a computer program capable of modeling both DNA-binding sites and the peptides themselves (Desjarlais & Berg, PNAS 90:2256-2260 (1993), PNAS 91:11099-11103 (1994) or by phage display methods. In one embodiment, the linker comprises the following amino acid sequence: GSTSGSGKPGSGEGSTKG (SEQ ID NO: 36) (Cooper et al., Blood, 101(4): 1637-1644 (2003)).

In particular embodiments, the binding domain of the CAR is followed by one or more "spacer domains," which refers to the region that moves the antigen binding domain away from the effector cell surface to enable proper cell/cell contact, antigen binding and activation (Patel et al., Gene Therapy, 1999; 6: 412-419). The hinge domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

The binding domain of the CAR is generally followed by one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region. Illustrative hinge domains suitable for use in the CARs described herein include the hinge region derived from the extracellular regions of type 1 membrane proteins such as CD8α, CD4, CD28 and CD7, which may be wild-type hinge regions from these molecules or may be altered. In another embodiment, the hinge domain comprises a CD8α hinge region.

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source. The TM domain may be derived from (i.e., comprise at least the transmembrane region(s) of) the alpha, beta or zeta chain of the T-cell receptor, CD3ε, CD3ζ, CD4, CD5, CD8α, CD9, CD 16, CD22, CD27, CD28, CD33, CD37, CD45, CD64, CD80, CD86, CD 134, CD137, CD152, CD 154, and PD1.

In particular embodiments, CARs contemplated herein comprise an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. In some embodiments, a CAR contemplated herein comprises an intracellular signaling domain that comprises one or more "co-stimulatory signaling domain" and a "primary signaling domain."

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs. Illustrative examples of ITAM containing primary signaling domains that are of particular use in the invention include those derived from TCRζ, FcRγ, FcRβ, CD3γ, CD3δ, CD3ε, CD3ζ, CD22, CD79a, CD79b, and CD66d.

As used herein, the term, "co-stimulatory signaling domain," or "co-stimulatory domain", refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules include CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70. In one embodiment, a CAR comprises one or more co-stimulatory signaling domains selected from the group consisting of CD28, CD137, and CD134, and a CD3ζ primary signaling domain.

In some embodiments, an antibody-drug conjugate is provided. In particular embodiments, an antibody-drug conjugate comprises an antibody or antigen-binding portion thereof described herein. The drug can be, e.g., a chemotherapeutic molecule as described elsewhere herein. In some embodiments, the antibody-drug conjugate comprises a chemotherapeutic agent directly conjugated and/or bound to an antibody or antigen-binding portion thereof. In some embodiments, binding can be non-covalent, e.g., by hydrogen bonding, electrostatic, or van der Waals interactions; however, binding may also be covalent. By "conjugated" is meant the covalent linkage of at least two molecules. In some embodiments, the composition can be an antibody-drug conjugate.

In some embodiments, an antibody or antigen-binding portion thereof can be bound to and/or conjugated to multiple chemotherapeutic molecules. In some embodiments, an antibody-drug conjugate can be bound to and/or conjugated to multiple chemotherapeutic molecules. In some embodiments, the ratio of a given chemotherapeutic molecule to an antibody or antigen-binding portion thereof can be from about 1:1 to about 1,000:1, e.g., a single antibody reagent molecule can be linked to, conjugated to, etc. from about 1 to about 1,000 individual chemotherapeutic molecules.

In some embodiments, an antibody, or antigen-binding portion thereof, and the chemotherapeutic agent can be present in a scaffold material. Scaffold materials suitable for use in therapeutic compositions are known in the art and can include, but are not limited to, a nanoparticle; a matrix; a hydrogel; and a biomaterial, biocompatible, and/or biodegradable scaffold material. As used herein, the term "nanoparticle" refers to particles that are on the order of about $10^{-9}$ or one to several billionths of a meter. The term "nanoparticle" includes nanospheres; nanorods; nanoshells; and nanoprisms; these nanoparticles may be part of a nanonetwork.

The term "nanoparticles" also encompasses liposomes and lipid particles having the size of a nanoparticle. As used herein, the term "matrix" refers to a 3-dimensional structure comprising the components of a composition described herein (e.g., an antibody or antigen-binding portion thereof). Non-limiting examples of matrix structures include foams; hydrogels; electrospun fibers; gels; fiber mats; sponges; 3-dimensional scaffolds; non-woven mats; woven materials; knit materials; fiber bundles; and fibers and other similar formats (See, e.g., Rockwood et al. Nature Protocols 2011 6:1612-1631 and US Patent Publications 2011/0167602; 2011/0009960; 2012/0296352; and U.S. Pat. No. 8,172,901; each of which is incorporated by reference herein in its entirety). The structure of the matrix can be selected by one of skill in the art depending upon the intended application of the composition, e.g., electrospun matrices can have greater surface area than foams.

In some embodiments, the scaffold is a hydrogel. As used herein, the term "hydrogel" refers to a three-dimensional polymeric structure that is insoluble in water but which is capable of absorbing and retaining large quantities of water to form a stable, often soft and pliable, structure. In some embodiments, water can penetrate in between the polymer chains of the polymer network, subsequently causing swelling and the formation of a hydrogel. In general, hydrogels are superabsorbent. Hydrogels have many desirable properties for biomedical applications. For example, they can be made nontoxic and compatible with tissue, and they are highly permeable to water, ions, and small molecules. Hydrogels are super-absorbent (they can contain over 99% water) and can be comprised of natural (e.g., silk) or synthetic polymers, e.g., PEG.

As used herein, "biomaterial" refers to a material that is biocompatible and biodegradable. As used herein, the term "biocompatible" refers to substances that are not toxic to cells. In some embodiments, a substance is considered to be "biocompatible" if its addition to cells in vitro results in less than or equal to approximately 20% cell death. In some embodiments, a substance is considered to be "biocompatible" if its addition to cells in vivo does not induce inflammation and/or other adverse effects in vivo. As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

In some embodiments, the technology described herein relates to a nucleic acid encoding an antibody, antigen-binding portion thereof, or CAR as described herein. In some embodiments, the nucleic acid comprises the sequence of SEQ ID NOs: 8-11. In some embodiments, the nucleic acid is a cDNA.

As used herein, the term "nucleic acid" or "nucleic acid sequence" refers to a polymeric molecule incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. In some embodiments, the nucleic acid can be a cDNA, e.g., a nucleic acid lacking introns.

In some embodiments, a nucleic acid encoding an antibody, antigen-binding portion thereof, or CAR as described herein is comprised by a vector. In some of the aspects described herein, a nucleic acid sequence encoding an antibody, antigen-binding portion thereof, or CAR as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g., 5' untranslated (5'UTR) or "leader" sequences and 3'

UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding an antibody, antigen-binding portion thereof, or CAR as described herein in place of non-essential viral genes. The vector and/or particle may be utilized for the purpose of transferring any nucleic acids into cells either in vitro or in vivo. Numerous forms of viral vectors are known in the art.

In particular embodiments, a cell (e.g., an immune cell) is transduced with a retroviral vector, e.g., a lentiviral vector, encoding a CAR. For example, an immune effector cell is transduced with a vector encoding a CAR that comprises an anti-CSPG4 antibody or antigen binding portion thereof that binds a CSPG4 polypeptide, with an intracellular signaling domain of CD3ζ, CD28, 4-1BB, Ox40, or any combinations thereof. Thus, these transduced cells can elicit a CAR-mediated cytotoxic response.

Retroviruses are a common tool for gene delivery (Miller, 2000, Nature. 357: 455-460). In particular embodiments, a retrovirus is used to deliver a polynucleotide encoding a chimeric antigen receptor (CAR) to a cell. As used herein, the term "retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include, but are not limited to: Moloney murine leukemia virus (M-MuLV), Moloney murine sarcoma virus (MoMSV), Harvey murine sarcoma virus (Ha-MuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred. In particular embodiments, a lentivirus is used to deliver a polynucleotide comprising a CAR to a cell.

Retroviral vectors and more particularly lentiviral vectors may be used in practicing particular embodiments of the present invention. Accordingly, the term "retrovirus" or "retroviral vector", as used herein is meant to include "lentivirus" and "lentiviral vectors" respectively.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In one aspect, a cell comprising an isolated antibody, antigen-binding portion thereof, or CAR as described herein is provided. In some embodiments, the isolated antibody, antigen-binding portion thereof, or CAR as described herein is expressed on the cell surface. In some embodiments, the cell comprises a nucleic acid encoding an isolated antibody, antigen-binding portion thereof, or CAR as described herein In some embodiments, the cell is an immune cell. As used herein, "immune cell" refers to a cell that plays a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. In some embodiments, the cell is a T cell; a NK cell; a NKT cell; lymphocytes, such as B cells and T cells; and myeloid cells, such as monocytes, macrophages, eosinophils, mast cells, basophils, and granulocytes.

Aspects of the technology described herein relate to compositions comprising an antibody, antigen-binding portion thereof, or CAR as described herein or a nucleic acid encoding an antibody, antigen-binding portion thereof, or CAR as described herein or a cell or composition as described herein. In some embodiments, the composition is a pharmaceutical composition. As used herein, the term "pharmaceutical composition" refers to the active agent in combination with a pharmaceutically acceptable carrier accepted for use in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance or maintain the effectiveness of the active ingredient. The therapeutic composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

In some embodiments, the composition comprising an antibody, antigen-binding portion thereof, or CAR as described herein or a nucleic acid encoding an antibody, antigen-binding portion thereof, or CAR as described herein can be a lyophilisate.

In some embodiments, the technology described herein relates to a syringe or catheter, including an organ-specific catheter (e.g., renal catheter, biliary catheter, cardiac catheter, etc.), comprising a therapeutically effective amount of a composition described herein.

As used herein, the phrase "therapeutically effective amount", "effective amount" or "effective dose" refers to an amount that provides a therapeutic or aesthetic benefit in the treatment, prevention, or management of a tumor or malignancy, e.g., an amount that provides a statistically significant decrease in at least one symptom, sign, or marker of a tumor or malignancy. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents In one aspect, described herein is a method of inhibiting or killing a CSPG4+ cell, the method comprising contacting the cell with an isolated antibody, antigen-binding portion thereof, or CAR as described herein, a nucleic acid encoding such polypeptides, a cell comprising such a polypeptide or nucleic acid, or a composition comprising such a polypeptide or nucleic acid. Inhibiting a CSPG4+ cell can comprise inhibiting the metabolic activity, metastasis, and/or proliferation of the cell. Assays for measuring metabolic activity, metastasis (e.g., migration assays) and proliferation are well known in the art. Similarly, assays for measuring killing of CSPG4+ cells, e.g., cell viability assays are well known in the art.

As used herein, a "CSPG4+" cell is a cell expressing an increased level of CSPG4+, e.g., as compared to a healthy cell of the same type or an average level of CSPG4 found in healthy cells of the same type. In some embodiments, an increased level of CSPG4 can be a level which is at least 1.5× the level found in a reference, e.g., 1.5×, 2×, 3×, 4×, 5× or greater than the reference level.

In one aspect, the technology described herein relates to a method comprising administering an antibody, antigen-binding portion thereof, or CAR as described herein or a nucleic acid encoding an antibody, antigen-binding portion thereof, or CAR as described herein to a subject. In some embodiments, the subject is in need of treatment for a cancer and/or malignancy. In some embodiments, the subject is in need of treatment for: melanoma; breast cancer; triple negative breast cancer; glioma; head and neck cancer; head and neck squamous cell carcinoma; carcinoma; mesothelioma; chordoma; condrosarcoma; sarcoma; leukemia; 11q23 positive acute leukemia; acute leukemia; and/or a CSPG4+ cancer or tumor. In some embodiments, the method is a method of treating a subject. In some embodiments, the method is a method of treating a cancer in a subject.

In one aspect, described herein is a method of treating cancer in a subject in need thereof, the method comprising administering a cell as described herein, e.g., a cell comprising an antibody, antigen-binding portion thereof, or CAR as described herein. In some embodiments, the cell is an immune cell.

In one aspect, described herein is a method of treating cancer in a subject in need thereof, the method comprising administering a nucleic acid as described herein or an immune cell comprising the nucleic acid to the subject, wherein the subject's immune cells are caused to express the polypeptide encoded by the nucleic acid. In some embodiments, the immune cell is a T cell. Nucleic acids can be targeted to particular cell types by, e.g., use of a cell-type specific promoter and/or a composition that selectively binds to the desired cell type. For example, conjugation of a nucleic acid to an aptamer can permit targeted delivery (McNamara, J O., et al. (2006) Nat. Biotechnol. 24:1005-1015). In an alternative embodiment, the nucleic acid can be delivered using drug delivery systems such as a nanoparticle, a dendrimer, a polymer, liposomes, or a cationic delivery system. Positively charged cationic delivery systems facilitate binding of an nucleic acid molecule (negatively charged) and also enhance interactions at the negatively charged cell membrane to permit efficient uptake of a nucleic acid by the cell. Cationic lipids, dendrimers, or polymers can either be bound to a nucleic acid, or induced to form a vesicle or micelle (see e.g., Kim S H., et al. (2008) Journal of Controlled Release 129(2):107-116) that encases a nucleic acid. The formation of vesicles or micelles further prevents degradation of the nucleic acid when administered systemically. Methods for making and administering cationic-inhibitory nucleic acid complexes are well within the abilities of one skilled in the art (see e.g., Sorensen, D R., et al. (2003) J. Mol. Biol 327:761-766; Verma, U N., et al. (2003) Clin. Cancer Res. 9:1291-1300; Arnold, A S et al. (2007) J. Hypertens. 25:197-205, which are incorporated herein by reference in their entirety). Some non-limiting examples of drug delivery systems useful for systemic delivery of nucleic acids include DOTAP (Sorensen, D R., et al. (2003), supra; Verma, U N., et al. (2003), supra), Oligofectamine, "solid nucleic acid lipid particles" (Zimmermann, T S., et al. (2006) Nature 441:111-114), cardiolipin (Chien, P Y., et al. (2005) Cancer Gene Ther. 12:321-328; Pal, A., et al. (2005) Int J. Oncol. 26:1087-1091), polyethyleneimine (Bonnet M E., et al. (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A., et al. (2007) Biochem. Soc. Trans. 35:61-67; Yoo, H., et al. (1999) Pharm. Res. 16:1799-1804). In some embodiments, a nucleic acid forms a complex with cyclodextrin for systemic administration. Methods for administration and pharmaceutical compositions of nucleic acids and cyclodextrins can be found in U.S. Pat. No. 7,427,605, which is herein incorporated by reference in its entirety. Targeted delivery of nucleic acids is described, for example in Ikeda and Taira Pharmaceutical Res 2006 23:1631-1640; Soutschek et al., Nature 2004 432:173-8 and Lorenze et al. Bioorg. Med. Chem. Lett. 14, 4975-4977 (2004); each of which is incorporated by reference herein in its entirety. By way of example, the nucleic acid can be targeted to immune cells by encapsulating the inhibitor in a liposome comprising ligands of receptors expressed on immune cells, e.g., TCRs. In some embodiments, the liposome can comprise aptamers specific for immune cells.

In some embodiments, the methods described herein relate to CAR-T cell therapy. CAR-T cell and related therapies relate to adoptive cell transfer of immune cells (e.g., T cells) expressing a CAR that binds specifically to a targeted cell type (e.g., cancer cells) to treat a subject. In some embodiments, the cells administered as part of the therapy can be autologous to the subject. In some embodiments, the cells administered as part of the therapy are not autologous to the subject. In some embodiments, the cells are engineered and/or genetically modified to express the CAR. Further discussion of CAR-T therapies can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs. Hemopoietic cancers, such as leukemia, are able to out-compete the normal hemopoietic compartments in a subject, thereby leading to hemopoietic failure (in the form of anemia, thrombocytopenia and neutropenia) ultimately causing death.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice. See, e.g., Freshney, CULTURE ANIMAL CELLS: MANUAL BASIC TECH. (3rd ed., 1994).

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patients or subjects include any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, various cancers. In addition, the methods described herein can be used to treat domesticated animals and/or pets. A subject can be male or female.

A subject can be one who has been previously diagnosed with or identified as suffering from or having a condition in need of treatment (e.g., a cancer) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. For example, a subject can be one who exhibits one or more risk factors for a condition or one or more complications related to a condition or a subject who does not exhibit risk factors. A "subject in need" of treatment for a particular condition can be a subject having that condition, diagnosed as having that condition, or at risk of developing that condition.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of a tumor or malignancy, delay or slowing of tumor growth and/or metastasis, and an increased lifespan as compared to that expected in the absence of treatment. As used herein, the term "administering," refers to the placement of an agent, including but not limited to, an antibody, antigen-binding portion thereof, or CAR as described herein or a nucleic acid encoding an antibody, antigen-binding portion thereof, or CAR, or a cell comprising such an agent, as described herein into a subject by a method or route which results in at least partial localization of the agents at a desired site. The pharmaceutical composition comprising an antibody, antigen-binding portion thereof, or CAR as described herein or a nucleic acid encoding an antibody, antigen-binding portion thereof, or CAR, or a cell comprising such an agent as described herein disclosed herein can be administered by any appropriate route which results in an effective treatment in the subject.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

It can generally be stated that a pharmaceutical composition comprising the cells, e.g., T cells or immune cells, described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present invention, particularly since all the infused cells will be redirected to a particular target antigen, lower numbers of cells, in the range of $10^6$/kilogram ($10^6$-$10^{11}$ per patient) may be administered. CAR expressing cell compositions may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MIP1α, etc.) as described herein to enhance induction of the immune response. In some embodiments, the dosage can be from about $1\times10^5$ cells to about $1\times10^8$ cells per kg of body weight. In some embodiments, the dosage can be from about $1\times10^6$ cells to about $1\times10^7$ cells per kg of body weight. In some embodiments, the dosage can be about $1\times10^6$ cells per kg of body weight. In some embodiments, one dose of cells can be administered. In some embodiments, the dose of cells can be repeated, e.g., once, twice, or more. In some embodiments, the dose of cells can be administered on, e.g., a daily, weekly, or monthly basis.

The dosage ranges for the agent depend upon the potency, and encompass amounts large enough to produce the desired effect e.g., slowing of tumor growth or a reduction in tumor size. The dosage should not be so large as to cause unacceptable adverse side effects. Generally, the dosage will vary with the age, condition, and sex of the patient and can be determined by one of skill in the art. The dosage can also be adjusted by the individual physician in the event of any complication. In some embodiments, the dosage ranges from 0.001 mg/kg body weight to 0.5 mg/kg body weight. In some embodiments, the dose range is from 5 μg/kg body weight to 100 μg/kg body weight. Alternatively, the dose range can be titrated to maintain serum levels between 1 μg/mL and 1000 μg/mL. For systemic administration, subjects can be administered a therapeutic amount, such as, e.g., 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

Administration of the doses recited above can be repeated. In some embodiments, the doses are given once a day, or multiple times a day, for example but not limited to three times a day. In a some embodiments, the doses recited above are administered daily for several weeks or months. The duration of treatment depends upon the subject's clinical progress and responsiveness to therapy.

In some embodiments, the dose can be from about 2 mg/kg to about 15 mg/kg. In some embodiments, the dose can be about 2 mg/kg. In some embodiments, the dose can be about 4 mg/kg. In some embodiments, the dose can be about 5 mg/kg. In some embodiments, the dose can be about 6 mg/kg. In some embodiments, the dose can be about 8 mg/kg. In some embodiments, the dose can be about 10 mg/kg. In some embodiments, the dose can be about 15 mg/kg. In some embodiments, the dose can be from about 100 mg/m$^2$ to about 700 mg/m$^2$. In some embodiments, the dose can be about 250 mg/m$^2$. In some embodiments, the dose can be about 375 mg/m$^2$. In some embodiments, the dose can be about 400 mg/m$^2$. In some embodiments, the dose can be about 500 mg/m$^2$.

In some embodiments, the dose can be administered intravenously. In some embodiments, the intravenous administration can be an infusion occurring over a period of from about 10 minute to about 3 hours. In some embodiments, the intravenous administration can be an infusion occurring over a period of from about 30 minutes to about 90 minutes.

In some embodiments the dose can be administered about weekly. In some embodiments, the dose can be administered weekly. In some embodiments, the dose can be administered weekly for from about 12 weeks to about 18 weeks. In some embodiments the dose can be administered about every 2 weeks. In some embodiments the dose can be administered about every 3 weeks. In some embodiments, the dose can be from about 2 mg/kg to about 15 mg/kg administered about every 2 weeks. In some embodiments, the dose can be from about 2 mg/kg to about 15 mg/kg administered about every 3 weeks. In some embodiments, the dose can be from about 2 mg/kg to about 15 mg/kg administered intravenously about every 2 weeks. In some embodiments, the dose can be from about 2 mg/kg to about 15 mg/kg administered intravenously about every 3 weeks. In some embodiments, the dose can be from about 200 mg/m$^2$ to about 400 mg/m$^2$ administered intravenously about every week. In some embodiments, the dose can be from about 200 mg/m$^2$ to about 400 mg/m$^2$ administered intravenously about every 2 weeks. In some embodiments, the dose can be from about 200 mg/m$^2$ to about 400 mg/m$^2$ administered intravenously about every 3 weeks. In some embodiments, a total of from about 2 to about 10 doses are administered. In some embodiments, a total of 4 doses are administered. In some embodiments, a total of 5 doses are administered. In some embodiments, a total of 6 doses are administered. In some embodiments, a total of 7 doses are administered. In some embodiments, a total of 8 doses are administered. In some embodiments, the administration occurs for a total of from about 4 weeks to about 12 weeks. In some embodiments, the administration occurs for a total of about 6 weeks. In some embodiments, the administration occurs for a total of about 8 weeks. In some embodiments, the administration occurs for a total of about 12 weeks. In some embodiments, the initial dose can be from about 1.5 to about 2.5 fold greater than subsequent doses.

In some embodiments, the dose can be from about 1 mg to about 2000 mg. In some embodiments, the dose can be about 3 mg. In some embodiments, the dose can be about 10 mg. In some embodiments, the dose can be about 30 mg. In some embodiments, the dose can be about 1000 mg. In some embodiments, the dose can be about 2000 mg. In some embodiments, the dose can be about 3 mg given by intravenous infusion daily. In some embodiments, the dose can be about 10 mg given by intravenous infusion daily. In some embodiments, the dose can be about 30 mg given by intravenous infusion three times per week.

A therapeutically effective amount is an amount of an agent that is sufficient to produce a statistically significant, measurable change in tumor size, tumor growth etc. (efficacy measurements are described below herein). Such effective amounts can be gauged in clinical trials as well as animal studies.

An agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, and can be delivered by peristaltic means, if desired, or by other means known by those skilled in the art. It is preferred that the compounds used herein are administered orally, intravenously or intramuscularly to a patient having cancer. Local administration directly to a tumor mass is also specifically contemplated.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

In some embodiments, the methods further comprise administering the pharmaceutical composition described herein along with one or more additional chemotherapeutic agents, biologics, drugs, or treatments as part of a combinatorial therapy. In some such embodiments, the chemotherapeutic agent biologic, drug, or treatment is selected from the group consisting of: radiation therapy, surgery, antibody reagents, and/or small molecules.

In some embodiments of the methods described herein, the methods further comprise administering one or more chemotherapeutic agents to the subject being administered the pharmaceutical composition described herein. Non-limiting examples of chemotherapeutic agents can include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any one of the above.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins, such as small molecule toxins or enzymatically active toxins of bacterial, fungal, plant or animal origin, including fragments and/or variants thereof.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g., see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology $2^{nd}$ Edition, 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). The bispecific and multispecific polypeptide agents described herein can be used in conjunction with additional chemotherapeutic agents.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

In some embodiments, the methods described herein can further comprise administering an additional immunotherapy to the subject. As used herein, "immunotherapy"

refers to a diverse set of therapeutic strategies designed to induce the patient's own immune system to fight the tumor, and include, but are not limited to, intravesical BCG immunotherapy for superficial bladder cancer, vaccines to generate specific immune responses, such as for malignant melanoma and renal cell carcinoma, the use of Sipuleucel-T for prostate cancer, in which dendritic cells from the patient are loaded with prostatic acid phosphatase peptides to induce a specific immune response against prostate-derived cells, administration of cytokines, growth factors and/or signaling molecules that stimulate one or more immune cell type (e.g., interleukins), ex vivo expansion and/or stimulation of lymphocytes and/or dendritic cell specific for a tumor antigen prior to reintroduction to the patient, imiquimod, adoptive cell transfer, and/or the methods described, e.g., in International Patent Publication WO 2003/063792 and U.S. Pat. No. 8,329,660. In some embodiments, the immunotherapy stimulates NK responses. In some embodiments, the immunotherapy is an adoptive cell transfer approach, i.e., adoptive immunotherapy.

In some embodiments, the methods described herein can further comprise administering an additional antibody, antigen-binding portion thereof, or T cell comprising a CAR to the subject. In some embodiments, the methods described herein can further comprise administering cytokine to the subject. Antibody- and cytokine-based therapies are known in the art and can include, by way of non-limiting example, alemtuzumab; bevacizumab; brentuximab vedotin; cetuximab; gemtuzumab; ibritumomab tiuxetan; ipilimumab; ofatumumab; pantibumumab; rituximab; tositumomab; trastuzumab; interleukin-2, and interferon-alpha.

The efficacy of a given treatment for cancer can be determined by the skilled clinician. However, a treatment is considered "effective treatment," as the term is used herein, if any one or all of the signs or symptoms of e.g., a tumor are altered in a beneficial manner or other clinically accepted symptoms are improved, or even ameliorated, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill in the art and/or described herein.

An effective amount for the treatment of a disease means that amount which, when administered to a mammal in need thereof, is sufficient to result in effective treatment as that term is defined herein, for that disease. Efficacy of an agent can be determined by assessing physical indicators of, for example cancer, e.g., tumor size, tumor mass, tumor density, angiogenesis, tumor growth rate, etc.

In one aspect, described herein is a method of detecting, prognosing, and/or diagnosing cancer, the method comprising detecting or measuring the level of CSPG4 in a sample obtained from a subject by contacting the sample with an antibody or antigen-binding portion thereof as described herein, wherein an increase in CSPG4 levels relative to a reference level indicates the subject has cancer, is at increased risk of developing cancer, or has a CSPG4+ cancer.

In one aspect, described herein is an assay comprising contacting a test sample obtained from the subject with an antibody or antigen-binding portion thereof as described herein, and detecting the presence or intensity of a signal which indicates the presence or level of CSPG4 in the sample; wherein an increase in the CSPG4 level relative to a reference level indicates the subject has a higher risk of having or developing cancer. In some embodiments, an increase in the CSPG4 level relative to a reference level indicates the subject has a higher risk of having or developing CSPG4+ cancer. In some embodiments, an increase in the CSPG4 level relative to a reference level indicates the subject has CSPG4+ cancer.

In one aspect, described herein is a method of identifying a subject in need of treatment for cancer, the method comprising: contacting a test sample obtained from the subject with an antibody or antigen-binding portion thereof as described herein, detecting the presence or intensity of a signal which indicates the presence or level of CSPG4 in the sample; and identifying the subject as being in need of treatment for cancer when the expression level of CSPG4 is increased relative to a reference level.

In one aspect, described herein is a method of determining if a subject is at risk for cancer, the method comprising: contacting a test sample obtained from the subject with an antibody or antigen-binding portion thereof as described herein, detecting the presence or intensity of a signal which indicates the presence or level of CSPG4 in the sample; comparing the level of CSPG4 in the sample to a reference level of CSPG4; determining that the subject is at risk for cancer when the level of CSPG4 is increased relative to a reference level; and determining that the subject is not at risk for cancer when the level of CSPG4 is not increased relative to a reference level.

In one aspect, described herein is a method of determining if a subject is likely to respond to treatment with anti-CSPG4 therapy, e.g., an anti-CSPG4 antibody or antigen binding portion thereof, or T cell comprising a CAR that binds CSPG4, the method comprising: contacting a test sample obtained from the subject with an antibody or antigen-binding portion thereof as described herein, detecting the presence or intensity of a signal which indicates the presence or level of CSPG4 in the sample; determining that the subject is likely to respond to treatment with anti-CSPG4 therapy when the level of CSPG4 is increased relative to a reference level; and determining that the subject is not likely to respond to treatment with anti-CSPG4 when the level of CSPG4 is not increased relative to a reference level.

In one aspect, described herein is a method of determining the efficacy of a treatment for cancer, the method comprising: (a) contacting a test sample obtained from the subject with an antibody or antigen-binding portion thereof as described herein and detecting the presence or intensity of a signal which indicates the presence or level of CSPG4 in the sample before administration of the treatment; (b) contacting a test sample obtained from the subject with an antibody or antigen-binding portion thereof as described herein and detecting the presence or intensity of a signal which indicates the presence or level of CSPG4 in the sample after administration of the treatment; (c) determining that the treatment is efficacious when the level determined in step (b) is decreased relative to the expression level determined in step (a); and (d) determining that the treatment is not efficacious when the expression level determined in step (b) is increased relative to the expression level determined in step (a).

In one aspect, described herein is a method of treatment for cancer comprising; contacting a test sample obtained from the subject with an antibody or antigen-binding portion thereof as described herein; detecting the presence or intensity of a signal which indicates the presence or level of CSPG4 in the sample; and treating the subject with an anti-CSPG4 therapy when the level of CSPG4 is increased relative to a reference level.

In one aspect, described herein is a method of treating cancer comprising; administering a therapeutically effective amount of an anti-CSPG4 therapy to a subject determined to be in need of treatment for cancer and further determined to have a level of CSPG4 that is increased relative to a reference level, wherein the anti-CSPG4 therapy comprises an isolated antibody, antigen-binding portion thereof, or T cell comprising a CAR that recognizes CSPG4; nucleic acid; cell; or composition as described herein.

In one aspect, described herein is a method of detecting CSPG4, the method comprising contacting a biological sample with an antibody or antigen-binding portion thereof as described herein, wherein reaction of the antibody or antigen-binding portion thereof with CSPG4 indicates the presence of CSPG4.

In one aspect, described herein is a method of detecting, quantitating, and/or isolating exosomes derived from CSPG4+ cells comprising contacting a sample comprising exosomes with an antibody or antigen-binding portion thereof as described herein or an antibody or antigen-binding portion thereof that is specific for CSPG4. In one aspect, described herein is a method of detecting or quantitating exosomes derived from CSPG4+ cells comprising contacting a sample comprising exosomes with an antibody or antigen-binding portion thereof as described herein or an antibody or antigen-binding portion thereof that is specific for CSPG4 and detecting the presence or intensity of a signal which indicates the presence or level of CSPG4 in the sample. In some embodiments, an increase in the level of CSPG4+ exosomes relative to a reference level indicates the subject has a higher risk of having or developing CSPG4+ cancer. In some embodiments, an increase in the level of CSPG4+ exosomes relative to a reference level indicates the subject has CSPG4+ cancer.

In some embodiments, the antibody or antigen-binding portion thereof can comprise one or more CDRs (e.g., one CDR, two CDRs, three CDRs, four CDRs, five CDRs, or six CDRs) having the sequence of a CDR selected from SEQ ID NOs: 1-6. In some embodiments, the antibody or antigen-binding portion thereof can comprise CDRs having the sequence of the CDRs of SEQ ID NOs: 1-6. In some embodiments, the antibody or antigen-binding portion thereof can be scFv-SK5 or a variant thereof. In some embodiments, the antibody or antigen-binding portion thereof can comprise one or more CDRs (e.g., one CDR, two CDRs, three CDRs, four CDRs, five CDRs, or six CDRs) of scFv-SK5. In some embodiments, the antibody or antigen-binding portion thereof can be scFv-FcC21 or a variant thereof. In some embodiments, the antibody or antigen-binding portion thereof can comprise one or more CDRs (e.g. one CDR, two CDRs, three CDRs, four CDRs, five CDRs, or six CDRs) of scFv-FcC21.

In one aspect, described herein is a method of isolating exosomes originating from CSPG4+ cells, the method comprising contacting a sample comprising exosomes with an antibody or antigen-binding portion thereof as described herein or an antibody or antigen-binding portion thereof that is specific for CSPG4; and isolating exosomes bound to the antibody or antigen-binding portion thereof. Antibodies and antigen-binding portions thereof may be labeled by any suitable means, such as affixing fluorescent moieties, radioactive labels, forming chemical conjugates, biotinylation, adding epitope tags, or any other moiety that facilitates detection and/or isolation. After exosomes have bound to one or more antibodies or antigen-binding portions thereof, the bound complex comprising the exosomes bound to the antibodies or antigen-binding portions thereof may be isolated. In some embodiments, the method further comprises separating bound exosomes from the unbound exosomes (and/or unbound portions of the sample) in order to isolate the exosomes originating from CSPG4+ cells. In some embodiments, the antibody or antigen-binding portion thereof is detectably labeled and/or epito-tagged. In some embodiments, the antibody or antigen-binding portion thereof is affixed (e.g. conjugated) to a solid support.

Methods for isolating bound complexes may include immunoprecipitation, ELISA, immunodetection, affinity purification, or detection of the label of the antibody and/or antigen-binding portion thereof. Detecting binding of the antibody and/or antigen-binding portion thereof and exosome can be performed with antibodies to the antibody and/or antigen-binding portion thereof, antibodies to the exosome, or antibodies that have been generated to recognize the bound complex.

In some embodiments, the sample comprising exosomes can be a sample obtained from a subject. In some embodiments, the CSPG4+ cells can be melanoma cells. In some embodiments, the CSPG4+ cells can be cancer cells. In some embodiments, the CSPG4+ cells can be malignant cells.

The quantitation, detection, and/or isolation of exosomes as described in the foregoing embodiments, can permit, e.g., monitoring of clinical response to therapy and/or disease progression and/or recurrence. By way of non-limiting example, an increase in CSPG4+ exosomes can indicate the progression of disease while a decrease in CSPG4+ exosomes can indicate a favorable response to therapy. In some embodiments, isolated exosomes obtained by the methods described herein (e.g. using CSPG4-specific antibodies and antigen-binding portions thereof) are shed by malignant cells and can be compared to exosomes shed by normal cells to, e.g. identify diagnostic biomarkers and/or to compare the structural and functional characteristics of malignant cell derived exosomes with those of normal cell derived exosomes.

In some embodiments, a sample comprising exosomes can be a sample selected from the group consisting of: a serum; plasma; urine; saliva; and tumor sample.

In any embodiment of the various aspects described herein, the expression level of CSPG4 can be the expression level in exosomes.

In some embodiments, the expression level of CSPG4 can be measured by determining the level of an expression product of the CSPG4 gene, e.g., a CSPG4 RNA transcript or a CSPG4 polypeptide. Such molecules can be isolated, derived, or amplified from a biological sample, such as a biofluid. In some embodiments, a detectable signal is generated by the antibody or antigen-binding portion thereof when a CSPG4 molecule is present. In some embodiments, the antibody or antigen-binding portion thereof is detectably labeled or capable of generating a detectable signal. In some embodiments, the level of the CSPG4 is determined using a method selected from the group consisting of: Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay. In some embodiments, the antibody or antigen-binding portion thereof is detectably labeled or generates a detectable signal. In some embodiments, the expression level of CSPG4 is normalized relative to the expression level of one or more reference genes or reference proteins. In some embodiments, the reference level of CSPG4 is the expression level of CSPG4 in a prior sample obtained from the subject.

In some embodiments, the level of CSPG4 can be the level of CSPG4 polypeptide. Detection of CSPG4 polypeptides can be according to any method known in the art. Immunological methods to detect CSPG4 polypeptides in accordance with the present technology include, but are not limited to antibody techniques such as immunohistochemistry, immunocytochemistry, flow cytometry, fluorescence-activated cell sorting (FACS), immunoblotting, radioimmunoassays, western blotting, immunoprecipitation, enzyme-linked immunosorbant assays (ELISA), and derivative techniques that make use of antibody reagents as described herein.

Immunochemical methods require the use of an antibody reagent specific for the target molecule (e.g., the antigen or in the embodiments described herein, a CSPG4 polypeptide. In some embodiments, the assays, methods, and/or systems described herein can comprise: an anti-CSPG4 antibody reagent. In some embodiments, the antibody reagent can be detectably labeled. In some embodiments, the antibody reagent can be attached to a solid support (e.g., bound to a solid support). In some embodiments, the solid support can comprise a particle (including, but not limited to an agarose or latex bead or particle or a magnetic particle), a bead, a nanoparticle, a polymer, a substrate, a slide, a coverslip, a plate, a dish, a well, a membrane, and/or a grating. The solid support can include many different materials including, but not limited to, polymers, plastics, resins, polysaccharides, silicon or silica based materials, carbon, metals, inorganic glasses, and membranes.

In one embodiment, an assay, method, and/or system as described herein can comprise an ELISA. In an exemplary embodiment, a first antibody reagent can be immobilized on a solid support (usually a polystyrene micro titer plate). The solid support can be contacted with a sample obtained from a subject, and the antibody reagent will bind ("capture") antigens for which it is specific (e.g., CSPG4). The solid support can then be contacted with a second labeled antibody reagent (e.g., a detection antibody reagent). The detection antibody reagent can, e.g., comprise a detectable signal, be covalently linked to an enzyme, or can itself be detected by a secondary antibody which is linked to an enzyme through bio-conjugation. The presence of a signal indicates that both the first antibody reagent immobilized on the support and the second "detection" antibody reagent have bound to an antigen, i.e., the presence of a signal indicated the presence of a CSPG4 molecule. Between each step the plate is typically washed with a mild detergent solution to remove any proteins or antibodies that are not specifically bound. After the final wash step the plate is developed by adding an enzymatic substrate to produce a visible signal, which indicates the quantity of CSPG4 polypeptides in the sample. Older ELISAs utilize chromogenic substrates, though newer assays employ fluorogenic substrates with much higher sensitivity. There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem. 22:895-904. These references are hereby incorporated by reference in their entirety.

In one embodiment, the assays, systems, and methods described herein can comprise a lateral flow immunoassay test (LFIA), also known as the immunochromatographic assay, or strip test to measure or determine the level of CSPG4 polypeptide in a sample. LFIAs are a simple device intended to detect the presence (or absence) of CSPG4 in a sample. There are currently many LFIA tests used for medical diagnostics either for home testing, point of care testing, or laboratory use. LFIA tests are a form of immunoassay in which the test sample flows along a solid substrate via capillary action. After the sample is applied to the test strip it encounters a colored antibody reagent which mixes with the sample, and if bound to a portion of the sample, transits the substrate encountering lines or zones which have been pretreated with a second antibody reagent. Depending upon the level of CSPG4 present in the sample the colored antibody reagent can become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water samples etc. Strip tests are also known as dip stick test, the name bearing from the literal action of "dipping" the test strip into a fluid sample to be tested. LFIA strip test are easy to use, require minimum training and can easily be included as components of point-of-care test (POCT) diagnostics to be used on site in the field. LFIA tests can be operated as either competitive or sandwich assays. Sandwich LFIAs are similar to sandwich ELISA. The sample first encounters colored particles which are labeled with antibody reagents specific for a target (e.g., a CSPG4-specific antibody reagent). The test line will also contain antibody reagents (e.g., a CSPG4-specific antibody reagent). The test line will show as a colored band in positive samples. In some embodiments, the lateral flow immunoassay can be a double antibody sandwich assay, a competitive assay, a quantitative assay or variations thereof. There are a number of variations on lateral flow technology. It is also possible to apply multiple capture zones to create a multiplex test.

A typical test strip consists of the following components: (1) sample application area comprising an absorbent pad (i.e. the matrix or material) onto which the test sample is applied; (2) conjugate or reagent pad—this contains antibody reagent(s) specific to the target which can be conjugated to colored particles (usually colloidal gold particles, or latex microspheres); (3) test results area comprising a reaction membrane—typically a hydrophobic nitrocellulose or cellulose acetate membrane onto which antibody reagents are immobilized in a line across the membrane as a capture zone or test line (a control zone may also be present, containing antibodies specific for the antibody reagents conjugated to the particles or microspheres); and (4) optional wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones. While not strictly necessary, most tests will incorporate a second line which contains an antibody that picks up free latex/gold in order to confirm the test has operated correctly.

The use of "dip sticks" or LFIA test strips and other solid supports has been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Three U.S. patents (U.S. Pat. No. 4,444,880, issued to H. Tom; U.S. Pat. No. 4,305,924, issued to R. N. Piasio; and U.S. Pat. No. 4,135,884, issued to J. T. Shen) describe the use of "dip stick" technology to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teaching of these "dip stick" technologies as necessary for the detection of CSPG4 polypeptides. In some embodiments, the dip stick (or LFIA) can be suitable for use with urine samples. In some embodiments, a dip stick can be suitable for use with blood samples.

Immunochemistry is a family of techniques based on the use of a specific antibody, wherein antibodies are used to specifically target molecules inside or on the surface of cells. In some embodiments, immunohistochemistry ("IHC") and immunocytochemistry ("ICC") techniques can be used to detect or measure the levels of CSPG4 polypeptide. IHC is the application of immunochemistry to tissue sections, whereas ICC is the application of immunochemistry to cells or tissue imprints after they have undergone specific cytological preparations such as, for example, liquid-based preparations. In some instances, signal amplification may be integrated into the particular protocol, wherein a secondary antibody, that includes a label, follows the application of an antibody reagent specific for platelets or leukocytes. Typically, for immunohistochemistry, tissue obtained from a subject and fixed by a suitable fixing agent such as alcohol, acetone, and paraformaldehyde, is sectioned and reacted with an antibody. Conventional methods for immunohistochemistry are described in Buchwalow and Bocker (Eds) "Immunohistochemistry: Basics and Methods" Springer (2010): Lin and Prichard "Handbook of Practical Immunohistochemistry" Springer (2011); which are incorporated by reference herein in their entireties. In some embodiments, immunocytochemistry may be utilized where, in general, tissue or cells obtained from a subject are fixed by a suitable fixing agent such as alcohol, acetone, and paraformaldehyde, to which is reacted an antibody. Methods of immunocytological staining of human samples is known to those of skill in the art and described, for example, in Burry "Immunocytochemistry: A Practical Guide for Biomedical Research" Springer (2009); which is incorporated by reference herein in its entirety.

In some embodiments, one or more of the antibody reagents described herein can comprise a detectable label and/or comprise the ability to generate a detectable signal (e.g., by catalyzing a reaction converting a compound to a detectable product). Detectable labels can comprise, for example, a light-absorbing dye, a fluorescent dye, or a radioactive label. Detectable labels, methods of detecting them, and methods of incorporating them into an antibody reagent are well known in the art.

In some embodiments, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the antibody reagent. Alternatively, a detectable label can be linked such as by directly labeling a molecule that achieves binding to the antibody reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection antibody is labeled with a fluorescent compound. When the fluorescently labeled antibody is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4', 7',4,7-hexachlorofiuorescein (HEX), 6-carboxy-4',5'-dichloro-2',7'-dimethoxyfiuorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g., Cy3, Cy5 and Cy7 dyes; coumarins, e.g umbelliferone; benzimide dyes, e.g., Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc; BODIPY dyes and quinoline dyes.

In some embodiments, a detectable label can be a radiolabel including, but not limited to $^{3}$H, $^{125}$I, $^{35}$S, $^{14}$C, $^{32}$P, and $^{33}$P.

In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

In some embodiments, a detectable label is a chemiluminescent label, including, but not limited to lucigenin, luminol, luciferin, isoluminol, theromatic acridinium ester, imidazole, acridinium salt and oxalate ester.

In some embodiments, a detectable label can be a spectral colorimetric label including, but not limited to colloidal gold or colored glass or plastic (e.g., polystyrene, polypropylene, and latex) beads.

In some embodiments, antibodies can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, Calif.

An antibody reagent can also be detectably labeled using fluorescence emitting metals such as $^{152}$Eu, or others of the lanthanide series. These metals can be attached to the antibody reagent using such metal chelating groups as diethylenetriaminepentaacetic acid (DTPA) or ethylenediaminetetraacetic acid (EDTA).

The assays and methods as described herein can relate to determining if a subject has an increased level of CSPG4 relative to a reference level. In some embodiments, the reference level of CSPG4 can be the level of CSPG4 in a healthy subject not having, or not diagnosed as having, e.g., cancer. In some embodiments, the reference level can be the level in a sample of similar cell type, sample type, sample processing, and/or obtained from a subject of similar age, sex and other demographic parameters as the sample/subject for which the level of CSPG4 is to be determined. In some embodiments, the test sample and control reference sample are of the same type, that is, obtained from the same biological source, and comprising the same composition, e.g., the same number and type of cells and/or type of sample material. Accordingly, in some embodiments, the level of CSPG4 which is increased can vary as demographic factors such as age, gender, genotype, environmental factors, and individual medical histories vary. In some embodiments, the reference level can comprise the level of CSPG4 (e.g., CSPG4 polypeptide) in a sample of the same type taken from a subject not exhibiting any signs or symptoms of, e.g., cancer. In some embodiments, the reference expression level of CSPG4 can be the expression level of CSPG4 in a prior sample obtained from the subject. This permits a direct analysis of any change in levels in that individual.

In some embodiments, a level of CSPG4 can be increased relative to a reference level if the level of CSPG4 is at least 1.25× the reference level, e.g., at least 1.25×, at least 1.5×, at least 2×, at least 3×, at least 4×, at least 5×, at least 6×, or greater of the reference level. In some embodiments, the expression level of CSPG4 can be normalized relative to the expression level of one or more reference genes or reference proteins. In some embodiments, the expression level of CSPG4 can be normalized relative to a reference value.

In some embodiments, the expression level of no more than 20 other genes is determined. In some embodiments, the expression level of no more than 10 other genes is determined.

The term "sample" or "test sample" as used herein denotes a sample taken or isolated from an organism, e.g., a urine sample from a subject. Exemplary biological samples include, but are not limited to, a biofluid sample; serum; plasma; urine; saliva; and/or tumor sample, etc. The term also includes a mixture of the above-mentioned samples. The term "test sample" also includes untreated or pretreated (or pre-processed) biological samples. In some embodiments, a test sample can comprise cells from a subject. As used herein, the term "biofluid" refers to any fluid obtained from a biological source and includes, but is not limited to, blood, urine, and bodily secretions.

The test sample can be obtained by removing a sample from a subject, but can also be accomplished by using a previously isolated sample (e.g., isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, prepared by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of CSPG4 as described herein.

In some embodiments, the methods, assays, and systems described herein can further comprise a step of obtaining a test sample from a subject. In some embodiments, the subject can be a human subject.

In some embodiments, the methods, assays, and systems described herein can comprise creating a report based on the level of CSPG4. In some embodiments, the report denotes raw values for CSPG4 in the test sample (plus, optionally, the level of CSPG4 in a reference sample) or it indicates a percentage or fold increase in CSPG4 as compared to a reference level, and/or provides a signal that the subject is at risk of having, or not having cancer.

As used herein "at risk of having" refers to at least a 2-fold greater likelihood of having a particular condition as compared to a subject that did not have an elevated and/or increased level of CSPG4, e.g., a 2-fold, or 2.5-fold, or 3-fold, or 4-fold, or greater risk.

In some embodiments, the assay or method can further comprise the step of administering an anti-CSPG4 therapy. In some embodiments, the anti-CSPG4 therapy comprises an isolated antibody, antigen-binding portion thereof, or CAR or CAR T cell; nucleic acid; cell; or composition as described herein.

In one aspect, described herein is a kit comprising a composition as described herein, e.g., a composition comprising an antibody, antigen-binding portion thereof, or CAR as described herein. A kit is any manufacture (e.g., a package or container) comprising at least one reagent, e.g., an antibody, the manufacture being promoted, distributed, or sold as a unit for performing the methods described herein.

The kits described herein can optionally comprise additional components useful for performing the methods described herein. By way of example, the kit can comprise fluids (e.g., buffers) suitable for composition comprising an antibody, antigen-binding portion thereof, or CAR as described herein, an instructional material which describes performance of a method as described herein, and the like. A kit can further comprise devices and/or reagents for delivery of the composition as described herein. Additionally, the kit may comprise an instruction leaflet and/or may provide information as to the relevance of the obtained results.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments or portions thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated." The terms "purified" or "substantially purified" refer to an isolated nucleic acid or polypeptide that is at least 95% by weight the subject nucleic acid or polypeptide, including, for example, at least 96%, at least 97%, at least 98%, at least 99% or more. In some embodiments, the antibody, antigen-binding portion thereof, or CAR described herein is isolated. In some embodiments, the antibody, antigen-binding portion thereof, or CAR described herein is purified.

As used herein, "engineered" refers to the aspect of having been manipulated by the hand of man. For example, an antibody, antigen-binding portion thereof, or CAR is considered to be "engineered" when the sequence of the antibody, antigen-binding portion thereof, or CAR is manipulated by the hand of man to differ from the sequence of an antibody as it exists in nature. As is common practice and is understood by those in the art, progeny and copies of an engineered polynucleotide and/or polypeptide are typically still referred to as "engineered" even though the actual manipulation was performed on a prior entity.

The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof as described in Kabat et al. (1971) Ann. NY Acad, Sci. 190:382-391 and/or Kabat, E. A., et al. (1991) Sequences of Proteins of Immunological Interest, Fifth Edition, U.S. Department of Health and Human Services, NIH Publication No. 91-3242.

As used herein, an "epitope" can be formed on a polypeptide both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics.

"Avidity" is the measure of the strength of binding between an antigen-binding molecule (such as an antibody or antigen-binding portion thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody or portion of an antibody as described herein) will bind to their cognate or specific antigen with a dissociation constant (KD of $10^{-5}$ to $10^{-12}$ moles/liter or less, such as $10^{-7}$ to $10^{-12}$ moles/liter or less, or $10^{-8}$ to $10^{-12}$ moles/liter (i.e., with an association constant (KA) of $10^5$ to $10^{12}$ liter/moles or more, such as $10^7$ to $10^{12}$ liter/moles or $10^8$ to $10^{12}$ liter/moles). Any KD value greater than $10^{-4}$ mol/liter (or any KA value lower than $10^4$ M$^{-1}$) is generally considered to indicate non-specific binding. The KD for biological interactions which are considered meaningful (e.g., specific) are typically in the range of $10^{-10}$ M (0.1 nM) to $10^{-5}$ M (10000 nM). The stronger an interaction, the lower is its KD. For example, a binding site on an antibody or portion thereof described herein will bind to the desired antigen with an affinity less than 500 nM, such as less than 200 nM, or less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of an peptide (e.g., an antibody, CAR or portion thereof) described herein to bind to a target, such as an antigen present on the cell-surface of a cancer cell, with a KD $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. A polypeptide specifically bound to a target is not displaced by a non-similar competitor. In certain embodiments, an antibody, antigen-binding portion thereof, or CAR is said to specifically bind an antigen when it preferentially recognizes its target antigen in a complex mixture of proteins and/or macromolecules.

In some embodiments, a reagent that binds specifically to CSPG4 binds specifically to CSPG4 as compared to other cell surface proteins. In some embodiments, a reagent that binds specifically to CSPG4 binds specifically to CSPG4 as compared to other CSPGs, e.g., CSPG1-3 or CSPG5.

In some embodiments, an antibody, antigen-binding portion thereof, and/or CAR as described herein binds to CSPG4 with a dissociation constant ($K_D$) of $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. In some embodiments, an antibody, antigen-binding portion thereof, and/or CAR as described herein binds to CSPG4 with a dissociation constant ($K_D$) of from about $10^{-5}$ M to $10^{-6}$ M. In some embodiments, an antibody, antigen-binding portion thereof, and/or CAR as described herein binds to CSPG4 with a dissociation constant ($K_D$) of from about $10^{-6}$ M to $10^{-7}$ M. In some embodiments, an antibody, antigen-binding portion thereof, and/or CAR as described herein binds to CSPG4 with a dissociation constant ($K_D$) of from about $10^{-7}$ M to $10^{-8}$ M. In some embodiments, an antibody, antigen-binding portion thereof, and/or CAR as described herein binds to CSPG4 with a dissociation constant ($K_D$) of from about $10^{-8}$ M to $10^{-9}$ M. In some embodiments, an antibody, antigen-binding portion thereof, and/or CAR as described herein binds to CSPG4 with a dissociation constant ($K_D$) of from about $10^{-9}$ M to $10^{-10}$ M. In some embodiments, an antibody, antigen-binding portion thereof, and/or CAR as described herein binds to CSPG4 with a dissociation constant ($K_D$) of from about $10^{-10}$ M to $10^{-11}$ M. In some embodiments, an antibody, antigen-binding portion thereof, and/or CAR as described herein binds to CSPG4 with a dissociation constant ($K_D$) of from about $10^{-11}$ M to $10^{-12}$ M. In some embodiments, an antibody, antigen-binding portion thereof, and/or CAR as described herein binds to CSPG4 with a dissociation constant ($K_D$) of less than $10^{-12}$ M.

Also encompassed herein is an antibody or antigen-binding portion thereof that competes with the scFV SK5 construct described herein for binding to CSPG4 and has a $K_D$ for CSPG4 of $10^{-5}$ M or less, e.g., $10^{-6}$ M or less, $10^{-7}$ M or less, $10^{-8}$ M or less, $10^{-9}$ M or less, $10^{-10}$ M or less, $10^{-11}$ M or less or $10^{-12}$ M or less.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference).

Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

As used herein, the term "CDR" refers to the complementarity determining regions within antibody variable sequences. There are three CDRs in each of the variable regions of the heavy chain and of the light chain, which are designated CDR1, CDR2 and CDR3, for each of the variable regions. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Other boundaries defining CDRs overlapping with the Kabat CDRs have been described by Padlan (FASEB J. 9:133-139 (1995)) and MacCallum (J Mol Biol 262(5):732-45 (1996)) and Chothia (J. Mol. Biol. 196:901-917 (1987) and Nature 342:877-883 (1989)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat defined CDRs.

Light and heavy chain variable regions contain a "framework" region interrupted by three hypervariable regions, also called "complementarity-determining regions" or "CDRs." The CDRs can be defined or identified by conventional methods, such as by sequence according to Kabat et al. (Wu, T T and Kabat, E. A., J Exp Med. 132(2):211-50, (1970); Borden, P. and Kabat E. A., PNAS, 84: 2440-2443 (1987); (see, Kabat et al., Sequences of Proteins of Immunological Interest, U.S. Department of Health and Human Services, 1991, which is hereby incorporated by reference), or by structure according to Chothia et al (Chothia, C. and Lesk, A. M., J Mol. Biol., 196(4): 901-917 (1987), Chothia, C. et al, Nature, 342: 877-883 (1989)).

Illustrative examples of rules for predicting light chain CDRs include: CDR-L1 starts at about residue 24, is preceded by a Cys, is about 10-17 residues, and is followed by a Trp (typically Trp-Tyr-Gln, but also, Trp-Leu-Gln, Trp-Phe-Gln, Trp-Tyr-Leu); CDR-L2 starts about 16 residues after the end of CDR-L1, is generally preceded by Ile-Tyr, but also, Val-Tyr, Ile-Lys, Ile-Phe, and is 7 residues; and CDR-L3 starts about 33 residues after the end of CDR-L2, is preceded by a Cys, is 7-11 residues, and is followed by Phe-Gly-XXX-Gly (XXX is any amino acid).

Illustrative examples of rules for predicting heavy chain CDRs include: CDR-H1 starts at about residue 26, is preceded by Cys-XXX-XXX-XXX, is 10-12 residues and is followed by a Trp (typically Trp-Val, but also, Trp-Ile, Trp-Ala); CDR-H2 starts about 15 residues after the end of CDR-H1, is generally preceded by Leu-Glu-Trp-Ile-Gly (SEQ ID NO: 38), or a number of variations, is 16-19 residues, and is followed by Lys/Arg-Leu/Ile/Val/Phe/Thr/Ala-Thr/Ser/Ile/Ala; and CDR-H3 starts about 33 residues after the end of CDR-H2, is preceded by Cys-XXX-XXX (typically Cys-Ala-Arg), is 3 to 25 residues, and is followed by Trp-Gly-XXX-Gly.

In one embodiment, light chain CDRs and the heavy chain CDR2 and CDR3 are determined according to the Kabat method, and heavy chain CDR1 is determined according to the AbM method, which is a comprise between the Kabat and Clothia methods, see e.g., Whitelegg N & Rees A R, Protein Eng. 2000 December; 13(12):819-24 and Methods Mol Biol. 2004; 248:51-91. Programs for predicting CDRs are publicly available, e.g., AbYsis (bioinf.org.uk/abysis/).

The sequences of the framework regions of different light or heavy chains are relatively conserved within a species, such as humans. The framework region of an antibody, that is the combined framework regions of the constituent light and heavy chains, serves to position and align the CDRs in three-dimensional space. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, the CDRs located in the variable domain of the heavy chain of the antibody are referred to as CDRH1, CDRH2, and CDRH3, whereas the CDRs located in the variable domain of the light chain of the antibody are referred to as CDRL1, CDRL2, and CDRL3. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). Illustrative examples of light chain CDRs that are suitable for use in the compositions and methods contemplated herein include, but are not limited to the CDR sequences set forth in SEQ ID NOs: 1-3 and 18-20. Illustrative examples of heavy chain CDRs that are suitable for use in the compositions and methods contemplated herein include, but are not limited to the CDR sequences set forth in SEQ ID NOs: 4-6 and 21-23.

The terms "antigen-binding portion" or "antigen-binding portion" of an antibody, used interchangeably herein, refer to one or more portions of an antibody as described herein, said portions) still having the binding affinities as defined above herein. Portions of a complete antibody have been shown to be able to carry out the antigen-binding function of an antibody. In accordance with the term "antigen-binding portion" of an antibody, examples of binding portions include (i) an Fab portion, i.e., a monovalent portion composed of the VL, VH, CL and CH1 domains; (ii) an F(ab')2 portion, i.e., a bivalent portion comprising two Fab portions linked to one another in the hinge region via a disulfide bridge; (iii) an Fd portion composed of the VH and CH1 domains; (iv) an Fv portion composed of the FL and VH domains of a single arm of an antibody; and (v) a dAb portion (Ward et al., (1989) Nature 341:544-546) consisting of a VH domain or of VH, CH1, CH2, DH3, or VH, CH2, CH3 (dAbs, or single domain antibodies, comprising only $V_L$ domains have also been shown to specifically bind to target epitopes). Although the two domains of the Fv portion, namely VL and VH, are encoded by separate genes, they may further be linked to one another using a synthetic linker, e.g., a poly-G4S amino acid sequence ('G4S' disclosed as SEQ ID NO: 12), and recombinant methods, making it possible to prepare them as a single protein chain in which the VL and VH regions combine in order to form monovalent molecules (known as single chain Fv (ScFv); see, for example, Bird et al. (1988) Science 242:423-426; and Huston et al. (1988) Proc. Natl. Acad. Sci. USA 85:5879-5883). The term "antigen-binding portion" of an antibody is also intended to comprise such single chain antibodies. Other forms of single chain antibodies such as "diabodies" are likewise included here. Diabodies are bivalent, bispecific antibodies in which VH and VL domains are expressed on a single polypeptide chain, but using a linker which is too short for the two domains being able to combine on the same chain, thereby forcing said domains to pair with complementary domains of a different chain and to form two antigen-binding sites (see, for example, Holliger, R, et al. (1993) Proc. Natl. Acad. Sci. USA 90:64446448; Poljak, R. J, et al. (1994) Structure 2:1121-1123). An immunoglobulin constant domain refers to a heavy or light chain constant domain. Human IgG heavy chain and light chain constant domain amino acid sequences are known in the art.

Furthermore, an antibody, antigen-binding portion thereof, or CAR as described herein may be part of a larger immunoadhesion molecule formed by covalent or noncovalent association of said antibody or antibody portion with one or more further proteins or peptides. Relevant to such immunoadhesion molecules are the use of the streptavidin core region in order to prepare a tetrameric scFv molecule (Kipriyanov, S. M., et al. (1995) Human Antibodies and Hybridomas 6:93-101) and the use of a cystein residue, a marker peptide and a C-terminal polyhistidinyl, e.g., hexahistidinyl tag ('hexahistidinyl tag' disclosed as SEQ ID NO: 13) in order to produce bivalent and biotinylated scFv molecules (Kipriyanov, S. M., et al. (1994) Mol. Immunol. 31:10471058).

In some embodiments, the antibody, antigen-binding portion thereof, or CAR described herein can be an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the ability to specifically bind the target antigen (e.g., CSPG4). Such conservatively modified variants are in addition to and do not exclude polymorphic variants, interspecies homologs, and alleles consistent with the disclosure.

In some embodiments, a conservatively modified variant of an antibody reagent can comprise alterations other than in the CDRs, e.g., a conservatively modified variant of an antibody reagent can comprise CDRs having the sequence of one or more of SEQ ID NOs 1-6. In some embodiments, a conservatively modified variant of an antibody reagent can comprise CDRs having the sequences of SEQ ID NOs: 1-6.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g., antigen-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H).

Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the antibody, antigen-binding portion thereof, and/or CAR as described herein can be a variant of a sequence described herein, e.g., a conservative substitution variant of an antibody polypeptide. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or portion thereof that retains activity, e.g., antigen-specific binding activity for the relevant target polypeptide, e.g., CSPG4. A wide variety of PCR-based site-specific mutagenesis approaches are also known in the art and can be applied by the ordinarily skilled artisan.

Examples of substitution variants include conservative substitution of amino acids, e.g., in a $V_H$ or $V_L$ domain, that do not alter the sequence of a CDR. A conservative substitution in a sequence not comprised by a CDR can be a substitution relative to a wild-type or naturally-occurring sequence, e.g., human or murine framework and/or constant regions of an antibody sequence.

A variant amino acid or DNA sequence preferably is at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g., BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties.

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments, the antibody or antigen-binding portion thereof is a fully human antibody. In some embodiments, the antibody, antigen-binding portion thereof, is a humanized antibody or antibody reagent. In some embodiments, the antibody or antigen-binding portion thereof, is a chimeric antibody or antibody reagent. In some embodiments, the antibody, antigen-binding portion thereof, is a recombinant polypeptide. In some embodiments, the CAR comprises an extracellular domain that binds CSPG4, wherein the extracellular domain comprises a humanized or chimeric antibody or antigen-binding portion thereof.

The term "human antibody" refers to antibodies whose variable and constant regions correspond to or are derived from immunoglobulin sequences of the human germ line, as described, for example, by Kabat et al. (see Kabat, et al. (1991) Sequences of Proteins of Immunological Interest, Fifth Edition, U.S. Department of Health and Human Services, NIH Publication No. 91-3242). However, the human antibodies can contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies as described herein have variable regions and may also contain constant regions derived from immunoglobulin sequences of the human germ line (see Kabat, E. A., et al. (1991) Sequences of Proteins of Immunological Interest, Fifth Edition, U.S. Department of Health and Human Services, NIH Publication No. 91-3242). According to particular embodiments, however, such recombinant human antibodies are subjected to in-vitro mutagenesis (or to a somatic in-vivo mutagenesis, if an animal is used which is transgenic due to human Ig sequences) so that the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both. Preferably, mutagenesis leads to an affinity to the target which is greater, and/or an affinity to non-target structures which is smaller than that of the parent antibody.

The term "chimeric antibody" refers to antibodies which contain sequences for the variable region of the heavy and light chains from one species and constant region sequences from another species, such as antibodies having murine heavy and light chain variable regions linked to human constant regions. Humanized antibodies have variable region framework residues substantially from a human antibody (termed an acceptor antibody) and complementarity determining regions substantially from a non-human antibody, e.g., a mouse-antibody, (referred to as the donor immunoglobulin). See, Queen et al., Proc Natl Acad Sci USA 86:10029-10033 (1989) and WO 90/07861, U.S. Pat. Nos. 5,693,762, 5,693,761, 5,585,089, 5,530,101 and Winter, U.S. Pat. No. 5,225,539, which are herein incorporated by reference in their entirety. The constant region(s), if present, are also substantially or entirely from a human immunoglobulin. The human variable domains are usually chosen from human antibodies whose framework sequences exhibit a high degree of sequence identity with the (murine) variable region domains from which the CDRs were derived. The heavy and light chain variable region framework residues can be substantially similar to a region of the same or different human antibody sequences. The human antibody sequences can be the sequences of naturally occurring human antibodies or can be consensus sequences of several human antibodies. See Carter et al., WO 92/22653, which is herein incorporated by reference in its entirety.

In some embodiments, the antibody reagents (e.g., antibodies or CARs) described herein are not naturally-occurring biomolecules. For example, a murine antibody raised against an antigen of human origin would not occur in nature absent human intervention and manipulation, e.g., manufacturing steps carried out by a human. Chimeric antibodies are also not naturally-occurring biomolecules, e.g., in that they comprise sequences obtained from multiple species and assembled into a recombinant molecule. In certain particular embodiments, the human antibody reagents described herein are not naturally-occurring biomolecules, e.g., fully human antibodies directed against a human antigen would be subject to negative selection in nature and are not naturally found in the human body.

Traditionally, monoclonal antibodies have been produced as native molecules in murine hybridoma lines. In addition to that technology, the methods and compositions described herein provide for recombinant DNA expression of monoclonal antibodies. This allows the production of humanized antibodies as well as a spectrum of antibody derivatives and fusion proteins in a host species of choice. The production of antibodies in bacteria, yeast, transgenic animals and chicken eggs are also alternatives for hybridoma-based production systems. The main advantages of transgenic animals are potential high yields from renewable sources.

Nucleic acid molecules encoding amino acid sequence variants of antibodies are prepared by a variety of methods known in the art. These methods include, but are not limited to preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, NY, 1982 and 1989), and Ausubel, 1987, 1993, and can be used to construct nucleic acid sequences which encode a monoclonal antibody molecule, antigen binding region thereof, or CAR.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art. See, e.g., Sambrook et al., 1989; Ausubel et al., 1987-1993.

Accordingly, the expression of an antibody, antigen-binding portion thereof, or CAR as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an antibody or portion thereof as described herein with a specified amino terminus sequence. Moreover, problems associated with retention of initiation codon-derived methionine residues in direct yeast (or bacterial) expression maybe avoided. Sabin et al., 7 Bio/Technol. 705 (1989); Miller et al., 7 Bio/Technol. 698 (1989). Any of a series of yeast gene expression systems incorporating promoter and termination elements from the actively expressed genes coding for glycolytic enzymes produced in large quantities when yeast are grown in mediums rich in glucose can be utilized to obtain recombinant antibodies or antigen-binding portions thereof as described herein. Known glycolytic genes can also provide very efficient transcriptional control signals. For example, the promoter and terminator signals of the phosphoglycerate kinase gene can be utilized.

Production of antibodies or antigen-binding portions thereof as described herein in insects can be achieved. For example, by infecting the insect host with a baculovirus engineered to express a transmembrane polypeptide by methods known to those of ordinary skill in the art. See Ausubel et al., 1987, 1993.

In some embodiments, the introduced nucleotide sequence is incorporated into a plasmid or viral vector capable of autonomous replication in the recipient host. Any of a wide variety of vectors can be employed for this purpose and are known and available to those or ordinary skill in the art. See, e.g., Ausubel et al., 1987, 1993. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in E. coli, for example. Other gene expression elements useful for the expression of cDNA encoding antibodies, antigen-binding portions thereof, or CARs include, but are not limited to (a) viral transcription promoters and their enhancer elements, such as the SV40 early promoter. (Okayama et al., 3 Mol. Cell. Biol. 280 (1983)), Rous sarcoma virus LTR (Gorman et al., 79 PNAS 6777 (1982)), and Moloney murine leukemia virus LTR (Grosschedl et al., 41 Cell 885 (1985)); (b) splice regions and polyadenylation sites such as those derived from the SV40 late region (Okayarea et al., 1983), and (c) polyadenylation sites such as in SV40 (Okayama et al., 1983). Immunoglobulin cDNA genes can be expressed as described by Liu et al., infra, and Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., 1 Protein Engin. 499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In some embodiments, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene is assembled in, or inserted into, an expression vector. Recipient cells capable of expressing the chimeric immunoglobulin chain gene product are then transfected singly with an antibody, antigen-binding portion thereof, or CAR, or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In some embodiments, the fused genes encoding the antibody, antigen-binding portion thereof, CAR, or chimeric H and L chains, or portions thereof are assembled in separate expression vectors that are then used to co-transfect a recipient cell. Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes. Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively the fused genes encoding chimeric H and L chains can be assembled on the same expression vector.

For transfection of the expression vectors and production of the chimeric, humanized, or composite human antibodies described herein, the recipient cell line can be a myeloma cell. Myeloma cells can synthesize, assemble and secrete immunoglobulins encoded by transfected immunoglobulin genes and possess the mechanism for glycosylation of the immunoglobulin. For example, in some embodiments, the recipient cell is the recombinant Ig-producing myeloma cell SP2/0 (ATCC # CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

An expression vector carrying a chimeric, humanized, or composite human antibody construct, antibody, antigen-binding portion thereof, and/or CAR as described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538 (1988), as known to one of ordinary skill in the art.

In some aspects, provided herein are methods and systems for the production of a humanized antibody, which is prepared by a process which comprises maintaining a host transformed with a first expression vector which encodes the light chain of the humanized antibody and with a second expression vector which encodes the heavy chain of the humanized antibody under such conditions that each chain is expressed and isolating the humanized antibody formed by assembly of the thus-expressed chains. The first and second expression vectors can be the same vector. Also provided herein are DNA sequences encoding the light chain or the heavy chain of the humanized antibody; an expression vector which incorporates a said DNA sequence; and a host transformed with a said expression vector.

Generating a humanized antibody from the sequences and information provided herein can be practiced by those of ordinary skill in the art without undue experimentation. In one approach, there are four general steps employed to humanize a monoclonal antibody, see, e.g., U.S. Pat. Nos. 5,585,089; 6,835,823; 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Usually the CDR regions in humanized antibodies and human antibody variants are substantially identical, and more usually, identical to the corresponding CDR regions in the mouse or human antibody from which they were derived. Although not usually desirable, it is sometimes possible to make one or more conservative amino acid substitutions of CDR residues without appreciably affecting the binding affinity of the resulting humanized immunoglobulin or human antibody variant. Occasionally, substitutions of CDR regions can enhance binding affinity.

In addition, techniques developed for the production of "chimeric antibodies" (see Morrison et al., Proc. Natl. Acad. Sci. 81:851-855 (1984); Neuberger et al., Nature 312:604-608 (1984); Takeda et al., Nature 314:452-454 (1985); which are incorporated by reference herein in their entireties) by splicing genes from a mouse, or other species, antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region, e.g., humanized antibodies.

The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells (WO 87/02671; which is incorporated by reference herein in its entirety). The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody, antigen-binding portion thereof, or CAR as described herein. Such functional activities include binding to cancer cells and/or anti-cancer activity. Additionally, a polypeptide having functional activity means the polypeptide exhibits activity similar, but not necessarily identical to, an activity of a reference antibody, antigen-binding portion thereof, or CAR as described herein, including mature forms, as measured in a particular assay, such as, for example, a biological assay, with or without dose dependency. In the case where dose dependency does exist, it need not be identical to that of the reference antibody, antigen-binding portion thereof, or CAR, but rather substantially similar to the dose-dependence in a given activity as compared to the reference antibody, antigen-binding portion thereof, or CAR as described herein (i.e., the candidate polypeptide will exhibit greater activity, or not more than about 25-fold less, about 10-fold less, or about 3-fold less activity relative to the antibodies, antigen-binding portions, and/or CARs described herein).

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any one of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An isolated antibody, antigen-binding portion thereof, or chimeric antigen receptor (CAR), the antibody, antigen-binding portion thereof, or CAR comprising any one of the heavy and light chain complimentarity determining regions (CDRs) selected from the group consisting of:
   a. a light chain CDR1 having the amino acid sequence of SEQ ID NO: 4 or 21;
   b. a light chain CDR2 having the amino acid sequence of SEQ ID NO: 5 or 22;
   c. a light chain CDR3 having the amino acid sequence of SEQ ID NO: 6 or 23;
   d. a heavy chain CDR1 having the amino acid sequence of SEQ ID NO: 1 or 18;
   e. a heavy chain CDR2 having the amino acid sequence of SEQ ID NO: 2 or 19; and
   f. a heavy chain CDR3 having the amino acid sequence of SEQ ID NO: 3 or 20.
2. The isolated antibody, antigen-binding portion thereof, or CAR of paragraph 1, comprising the light chain complimentarity determining regions (CDRs):
   a. a light chain CDR1 having the amino acid sequence of SEQ ID NO: 4 or 21;
   b. a light chain CDR2 having the amino acid sequence of SEQ ID NO: 5 or 22; and
   c. a light chain CDR3 having the amino acid sequence of SEQ ID NO: 6 or 23.
3. The isolated antibody, antigen-binding portion thereof, or CAR of any one of paragraphs 1-2, comprising the heavy chain complimentarity determining regions (CDRs):
   a. a heavy chain CDR1 having the amino acid sequence of SEQ ID NO: 1 or 18;
   b. a heavy chain CDR2 having the amino acid sequence of SEQ ID NO: 2 or 19; and
   c. a heavy chain CDR3 having the amino acid sequence of SEQ ID NO: 3 or 20.
4. The isolated antibody, antigen-binding portion thereof, or CAR of any one of paragraphs 1-3, comprising the complimentarity determining regions (CDRs):
   a. a light chain CDR1 having the amino acid sequence of SEQ ID NO: 4 or 21;
   b. a light chain CDR2 having the amino acid sequence of SEQ ID NO: 5 or 22;
   c. a light chain CDR3 having the amino acid sequence of SEQ ID NO: 6 or 23;
   d. a heavy chain CDR1 having the amino acid sequence of SEQ ID NO: 1 or 18;
   e. a heavy chain CDR2 having the amino acid sequence of SEQ ID NO: 2 or 19; and
   f. a heavy chain CDR3 having the amino acid sequence of SEQ ID NO: 3 or 20.
5. The isolated antibody, antigen-binding portion thereof, or CAR of any one of paragraphs 1-4, comprising the sequence of SEQ ID NO: 7, 24, or 25.
6. The isolated antibody, antigen-binding portion thereof, or CAR of any one of paragraphs 1-5, further comprising a conservative substitution in a sequence not comprised by a CDR.
7. The isolated antibody, antigen-binding portion thereof, or CAR of any one of paragraphs 1-16, wherein the antibody or polypeptide is selected from the group consisting of:
   an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody.
8. The isolated antibody, antigen-binding portion thereof, or CAR of any one of paragraphs 1-7, wherein the isolated antibody, antigen-binding portion thereof, or CAR is fully human.
9. The isolated antibody, antigen-binding portion thereof, or CAR of any one of paragraphs 1-7, wherein the isolated antibody, antigen-binding portion thereof, or CAR comprises fully human antigen-binding domains.
10. The isolated antibody, antigen-binding portion thereof, or CAR of any one of paragraphs 1-9, wherein the isolated antibody, antigen-binding portion thereof, or CAR specifically binds to CSPG4.
11. A nucleic acid encoding an isolated antibody, antigen-binding portion thereof, or CAR of any one of paragraphs 1-10.
12. The nucleic acid of paragraph 11, wherein one or more of the nucleic acid sequences comprises a sequence selected from SEQ ID NOs: 8-11.
13. The nucleic acid of any one of paragraphs 11-12, wherein the nucleic acid is a cDNA.
14. A cell comprising the isolated antibody, antigen-binding portion thereof, or CAR of any one of paragraphs 1-10, or the nucleic acid of any one of paragraphs 11-13.
15. The cell of paragraph 14, wherein the cell is an immune cell.
16. The cell of paragraph 15, wherein the cell is selected from the group consisting of:
   a T cell; a NK cell; and a NKT cell.
17. The cell of any one of paragraphs 14-16, wherein the isolated antibody, antigen-binding portion thereof, or CAR is expressed on the cell surface.
18. A composition comprising the isolated antibody, antigen-binding portion thereof, or CAR of any one of paragraphs 1-10, and a chemotherapeutic agent.
19. The composition of paragraph 18, wherein the antibody or antigen-binding portion thereof is conjugated to the chemotherapeutic agent.
20. A pharmaceutical composition comprising an isolated antibody, antigen-binding portion thereof, or CAR of any one of paragraphs 1-10, the nucleic acid of any one of paragraphs 11-13, the cell of any one of paragraphs 14-16, or the composition of any one of paragraphs 18-19 and a pharmaceutically acceptable carrier.
21. A method of inhibiting or killing a CSPG4+ cell, the method comprising contacting the CSPG4+ cell with an isolated antibody, antigen-binding portion thereof, or CAR of any one of paragraphs 1-10, the nucleic acid of any one of paragraphs 11-13, the cell of any one of paragraphs 14-16, or the composition of any one of paragraphs 18-19.
22. A method of treating cancer in a subject in need thereof, the method comprising administering a therapeutically effective amount of an isolated antibody, antigen-binding portion thereof, or CAR of any one of paragraphs 1-10, the nucleic acid of any one of paragraphs 11-13, the cell of any one of paragraphs 14-16, or the composition of any one of paragraphs 18-19.
23. A method of treating cancer in a subject in need thereof, the method comprising administering a cell of any one of paragraphs 14-16 to the subject.
24. A method of treating cancer in a subject in need thereof, the method comprising administering a nucleic acid of any one of paragraph 11-13 to the subject, wherein the subject's T-cells are caused to express the polypeptide encoded by the nucleic acid.
25. The method of any one of paragraphs 22-24, wherein the cancer is selected from the group consisting of:
   melanoma; breast cancer; triple negative breast cancer; glioma; head and neck cancer; head and neck squamous cell carcinoma; carcinoma; mesothelioma; chordoma; condrosarcoma; sarcoma; leukemia; 11q23 positive acute leukemia; acute leukemia; and a CSPG4+ cancer or tumor.
26. An assay comprising:
   contacting a test sample obtained from the subject with an antibody or antigen-binding portion thereof of any one of paragraphs 1-10; and
   detecting the presence or intensity of a signal which indicates the presence or level of CSPG4 in the sample;
   wherein an increase in the CSPG4 level relative to a reference level indicates the subject has a higher risk of having or developing cancer.
27. The assay of paragraph 26, wherein an increase in the CSPG4 level relative to a reference level indicates the subject has a higher risk of having or developing CSPG4+ cancer.
28. The assay of paragraph 26, wherein the increase in the CSPG4 level relative to a reference level indicates the subject has CSPG4+ cancer.
29. A method of identifying a subject in need of treatment for cancer, the method comprising:
   contacting a test sample obtained from the subject with an antibody or antigen-binding portion thereof of any one of paragraphs 1-10;
   detecting the presence or intensity of a signal which indicates the presence or level of CSPG4 in the sample;
   identifying the subject as being in need of treatment for cancer when the expression level of CSPG4 is increased relative to a reference level.
30. A method of determining if a subject is at risk for cancer, the method comprising:
   contacting a test sample obtained from the subject with an antibody or antigen-binding portion thereof of any one of paragraphs 1-10;
   detecting the presence or intensity of a signal which indicates the presence or level of CSPG4 in the sample;
   comparing the level of CSPG4 in the sample to a reference level of CSPG4;
   determining that the subject is at risk for cancer when the level of CSPG4 is increased relative to a reference level; and
   determining that the subject is not at risk for cancer when the level of CSPG4 is not increased relative to a reference level.
31. A method of determining if a subject is likely to respond to treatment with anti-CSPG4 therapy,
   contacting a test sample obtained from the subject with an antibody or antigen-binding portion thereof of any one of paragraphs 1-10;
   detecting the presence or intensity of a signal which indicates the presence or level of CSPG4 in the sample;
   determining that the subject is likely to respond to treatment with anti-CSPG4 therapy when the level of CSPG4 is increased relative to a reference level; and
   determining that the subject is not likely to respond to treatment with anti-CSPG4 when the level of CSPG4 is not increased relative to a reference level.
32. A method of determining the efficacy of a treatment for cancer, the method comprising:
   (a) contacting a test sample obtained from the subject with an antibody or antigen-binding portion thereof of any one of paragraphs 1-10 and detecting the presence or intensity of a signal which indicates the presence or level of CSPG4 in the sample before administration of the treatment;
   (b) contacting a test sample obtained from the subject with an antibody or antigen-binding portion thereof of any one of paragraphs 1-10 and detecting the presence or intensity of a signal which indicates the presence or level of CSPG4 in the sample after administration of the treatment;
   (c) determining that the treatment is efficacious when the level determined in step (b) is decreased relative to the expression level determined in step (a); and
   (d) determining that the treatment is not efficacious when the expression level determined in step (b) is increased relative to the expression level determined in step (a).
33. A method of treatment for cancer, the method comprising;
   contacting a test sample obtained from the subject with an antibody or antigen-binding portion thereof of any one of paragraphs 1-10;
   detecting the presence or intensity of a signal which indicates the presence or level of CSPG4 in the sample;
   treating the subject with an anti-CSPG4 therapy when the level of CSPG4 is increased relative to a reference level.
34. A method of treating cancer, the method comprising; administering a therapeutically effective amount of an anti-CSPG4 therapy to a subject determined to be in need of treatment for cancer and further determined to have a level of CSPG4 that is increased relative to a reference level.
35. A method of detecting CSPG4, the method comprising contacting a biological sample with an antibody or antigen-binding portion thereof of any one of paragraphs 1-10, wherein reaction of the antibody or antigen-binding portion thereof with CSPG4 indicates the presence of CSPG4.
36. The assay or method of any one of paragraphs 26-35, wherein a detectable signal is generated by the antibody or antigen-binding portion thereof when a CSPG4 molecule is present.

37. The assay or method of any one of paragraphs 26-36, wherein the antibody or antigen-binding portion thereof is detectably labeled or capable of generating a detectable signal.
38. The assay or method of any one of paragraphs 26-37, wherein the level of the CSPG4 is determined using a method selected from the group consisting of:
Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay.
39. The assay or method of any one of paragraphs 26-38, wherein the antibody or antigen-binding portion thereof is detectably labeled or generates a detectable signal.
40. The assay or method of any one of paragraphs 26-39, wherein the expression level of CSPG4 is normalized relative to the expression level of one or more reference genes or reference proteins.
41. The assay or method of any one of paragraphs 26-40, wherein the reference level of CSPG4 is the expression level of CSPG4 in a prior sample obtained from the subject.
42. The assay or method of any one of paragraphs 26-41, further comprising the step of administering an anti-CSPG4 therapy.
43. The assay or method of any one of paragraphs 26-42, wherein the anti-CSPG4 therapy comprises an isolated antibody, antigen-binding portion thereof, or CAR of any one of paragraphs 1-10, the nucleic acid of any one of paragraphs 11-13, the cell of any one of paragraphs 14-16, or the composition of any one of paragraphs 18-19.
44. The assay or method of any one of paragraphs 26-43, wherein the level of CSPG4 is the level of CSPG4 comprised by exosomes.
45. The assay or method of paragraph 44, further comprising a step of isolating exosomes from the sample.
46. The assay or method of any one of paragraphs 26-45, wherein the sample is selected from the group consisting of:
a serum; plasma; urine; saliva; and tumor sample.
47. A kit for performing the method or assay of any one of paragraphs 26-46 comprising an isolated antibody, or antigen-binding portion thereof of any one of paragraphs 1-10.
48. A chimeric antigen receptor (CAR) comprising: an extracellular domain that comprises an anti-CSPG4 antibody or antigen binding portion thereof that binds one or more epitopes of a human CSPG4 polypeptide; a transmembrane domain, one or more intracellular co-stimulatory signaling domains, and a primary signaling domain.
49. The CAR of paragraph 48, wherein the anti-CSPG4 antibody or antigen binding portion that binds the human CSPG4 polypeptide is selected from the group consisting of: a Camel Ig, Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody).
50. The CAR of any one of paragraphs 48-49, wherein the anti-CSPG4 antibody or antigen binding portion thereof comprises one or more CDRs as set forth in any one of SEQ ID NOs: 1-6 or 18-23.
51. The CAR of any one of paragraphs 48-50, wherein the transmembrane domain is from a polypeptide selected from the group consisting of: alpha, beta or zeta chain of the T-cell receptor, CD3ε, CD3ζ, CD4, CD5, CD8α, CD9, CD 16, CD22, CD27, CD28, CD33, CD37, CD45, CD64, CD80, CD86, CD 134, CD137, CD152, CD 154, and PD1.
52. The CAR of any one of paragraphs 48-51, wherein the one or more co-stimulatory signaling domains are from a co-stimulatory molecule selected from the group consisting of: CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70.
53. The CAR of any one of paragraphs 48-52, wherein the primary signaling domain is CD3ζ.
54. A polynucleotide encoding a CAR of any one of paragraphs 48-53.
55. A vector comprising the polynucleotide of paragraph 54.
56. The vector of paragraph 55, wherein the vector is a retroviral vector.
57. The vector of paragraph 55, wherein the vector is a lentiviral vector.
58. The vector of paragraph 57, wherein the lentiviral vector is selected from the group consisting essentially of: human immunodeficiency virus 1 (HIV-1); human immunodeficiency virus 2 (HIV-2), visna-maedi virus (VMV) virus; caprine arthritis-encephalitis virus (CAEV); equine infectious anemia virus (EIAV); feline immunodeficiency virus (FIV); bovine immune deficiency virus (BIV); and simian immunodeficiency virus (SIV).
59. An immune cell comprising the vector of any one of paragraphs 55-58.
60. The immune cell of paragraph 59, wherein the immune cell is selected from the group consisting of: a T lymphocyte and a natural killer (NK) cell.
61. A composition comprising the immune cell of paragraph 59 or paragraph 60 and a physiologically acceptable excipient.
62. A method of treating a cancer in a subject in need thereof, comprising administering to the subject a therapeutically effective amount of the composition of paragraph 61.
63. The method of paragraph 62, wherein the cancer is selected from the group consisting of:
melanoma; breast cancer; triple negative breast cancer; glioma; head and neck cancer; head and neck squamous cell carcinoma; carcinoma; mesothelioma; chordoma; condrosarcoma; sarcoma; leukemia; 11q23 positive acute leukemia; acute leukemia; and a CSPG4+ cancer or tumor.
64. An assay comprising:
contacting a sample comprising exosomes obtained from a subject with an antibody or antigen-binding portion thereof of any one of paragraphs 1-10; and
detecting the presence or intensity of a signal which indicates the presence or level of CSPG4 in the sample;
wherein an increase in the CSPG4 level relative to a reference level indicates the subject has a higher risk of having or developing cancer.

65. The assay of paragraph 64, further comprising a step of isolating the exosomes.
66. The assay of paragraph 65, wherein the step of isolating the exosomes is performed prior to contacting the sample with the antibody or antigen-binding portion thereof.
67. The assay of any one of paragraphs 64-66, wherein an increase in the CSPG4 level relative to a reference level indicates the subject has a higher risk of having or developing CSPG4+ cancer.
68. The assay of any one of paragraphs 64-66, wherein the increase in the CSPG4 level relative to a reference level indicates the subject has CSPG4+ cancer.
69. The assay of any one of paragraphs 64-68, wherein the sample is selected from the group consisting of: a serum; plasma; urine; saliva; and tumor sample.
70. A method of isolating exosomes originating from CSPG4+ cells, the method comprising:
    contacting a sample comprising exosomes with an antibody or antigen-binding portion thereof of any one of paragraphs 1-10 or an antibody or antigen-binding portion thereof specific for CSPG4; and
    isolating exosomes bound to an antibody or antigen-binding portion thereof.
71. The method of paragraph 70, wherein the antibody or antigen-binding portion thereof is detectably labeled and/or epitope-tagged.
72. The method of paragraph 71, wherein the antibody or antigen-binding portion thereof is conjugated to a solid support.

EXAMPLES

Example 1: CSPG4-Specific Human scFv SK5

Isolation of scFv SK5 by Panning a Semi-Synthetic Phage Display scFv Library.

Three rounds of panning were performed to isolate scFvs which bind to CSPG4+ human melanoma cell line SK-MEL-28 from a semi-synthetic phage display scFv library. Then single clones of scFv were tested for reactivity with SK-MEL-28 cells and CSPG4− B lymphoid cell line LG2, resulting in isolation of scFv SK5, which specifically reacted with SK-MEL-28 cells but not with LG2 cells.

scFv SK5 Specifically Recognizes CSPG4 Expressed on Cell Surface

Human melanoma cell line M14 which does not express CSPG4 and the cell line M14/CSPG4 which was stably transfected with the full length of CSPG4 plasmid DNA and expresses CSPG4 were used to test the specificity of scFvSK5 by flow analysis. The data indicating that scFvSK5 binds specifically to CSPG4+ M14/CSPG4 cells but not to CSPG4− M14 cells. The irrelevant scFv 119 was used as a negative control (FIG. 1).

Figure 2:
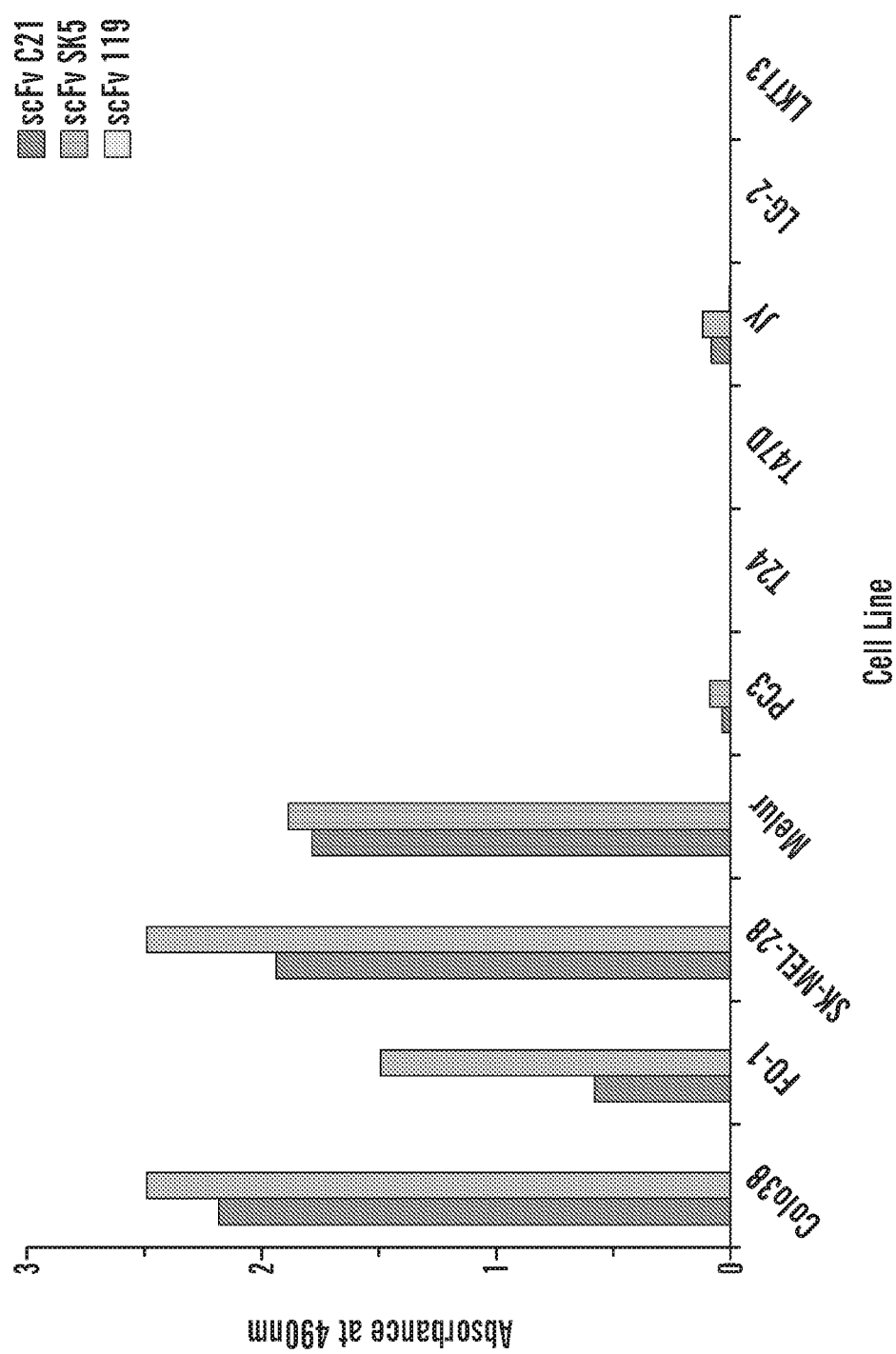
FIG. 2 demonstrates staining by scFv-FcC21 and scFv-SK5 of a panel of tumor cell lines. The human melanoma cell lines Colo38, FO-1, SK-MEL-38 and Melur; the prostate cancer cell lines PC3; the bladder cancer cell line T24; the breast cancer cell line T470; and the B lymphoid cell lines JY, LG2, and LKT13 were incubated with scFv SK5/mAb9E10 or isotype control scFv119/mAb9E10. Binding of scFv was detected with HRP-conjugated goat anti-mouse IgG (Fc-specific) antibodies and visualized using Ortho-Phenylenediamine (OPD) microwell peroxidase substrate. Results are expressed as optical density absorbance, which was determined at 490 nm on an ELISA plate reader.
Figure 8:
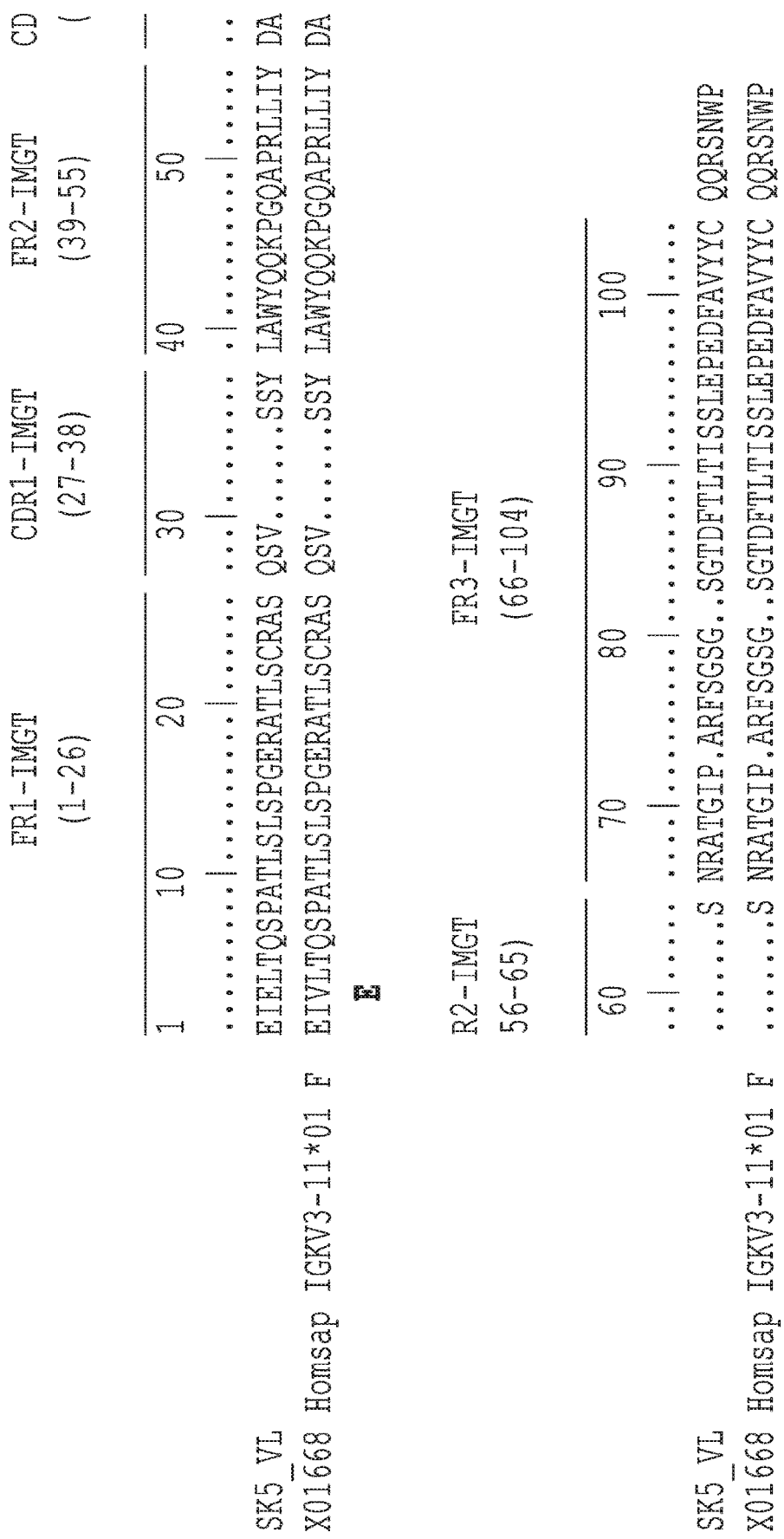
FIG. 8 depicts and alignment of V-region protein display (SEQ ID NOS 45 and 44, respectively, in order of appearance)

A panel of human cell lines were tested with scFv SK5 in a cell binding assay. The data indicating that scFv SK5 only reacts with CSPG4+ melanoma cell lines but not CSPG4− cell lines (FIG. 2). The scFvC21 and scFv 119 were used as positive and negative controls.

DNA Sequencing of scFv SK5

Single clones of plasmid DNA was prepared and sequenced for determination of nucleotide sequence (FIGS. 3 and 4).

Example 2

Chondroitin sulfate proteoglycan (CSPG) is a cell surface proteoglycan with biological and clinical significance, and was initially identified by mouse monoclonal antibodies (mAb) binding melanoma cells. Subsequently, it has been found that CSPG4 is expressed on melanoma (~85%), triple negative breast cancer (~70%), glioma (~70%), head and neck, squamous cell carcinoma (~60%), mesothelioma (50%), chordoma and chondrosarcoma (~50%) lesions, and on 11q23 positive acute leukemic (~50%) samples; cancer stem cells in breast cancer, head and neck cancer and melanoma cell lines, and tumor activated pericytes. However, CSPG4 has a restricted distribution in normal tissues. Moreover, CSPG4 promotes signaling pathways crucial for tumor cell proliferation, survival and migration. Its distinguished expression on cancer cells, cancer stem cells and tumor activated pericytes vs. normal tissues makes CSPG4 an ideal target for antibody- or T cell-based targeted therapies. To this end, described herein is a fully human scFv SK5 recognizing human CSPG4.

It is specifically contemplated herein that the compositions described herein (e.g., antibodies, antigen-binding portions thereof, antibody reagents, and CARs) can permit, e.g., CARs (e.g., for CAR-T therapy), whole human IgG as a naked monoclonal antibody for cancer treatment, and antibody-drug conjugates, e.g., for cancer treatment.

TABLE 1

CDRs (Using IMGT numbering scheme)

| Chain Identity | CDR Identity | Sequence | SEQ ID NO: |
|---|---|---|---|
| scFv SK5 Heavy Chain | CDR1 | GFTFDDYG | 1 |
|  | CDR2 | INWNGGST | 2 |
|  | CDR3 | ARGVLSRYFDY | 3 |
| scFv SK5 Light Chain | CDR1 | QSVSSY | 4 |
|  | CDR2 | DAS | 5 |
|  | CDR3 | QQRSNWPPA | 6 |

Table 2: CDRs (Using Kabat numbering scheme). In some embodiments of any of the aspects described herein, the following Kabat CDRs may be used instead of the IMGT CDRs described in Table 1.

| Chain Identity | CDR Identity | Sequence | SEQ ID NO: |
|---|---|---|---|
| scFv SK5 Heavy Chain | CDR1 | GFTFDDYGMS | 18 |
|  | CDR2 | GINWNGGSTGYADSVKG | 19 |
|  | CDR3 | GVLSRYFDY | 20 |
| scFv SK5 Light Chain | CDR1 | RASQSVSSYLA | 21 |
|  | CDR2 | DASNRAT | 22 |
|  | CDR3 | QQRSNWPPA | 23 |

TABLE 3

|  | Sequence | SEQ ID NO: |
|---|---|---|
| Light Chain Variable Region | EIELTQSPATLSLSPGERATLSCRASQ SVSSYLAWYQQKPGQAPRLLIYDASNR ATGIPARFSGSGSGTDFTLTISSLEPE DFAVYYCQQRSNWPPAFGGGTKVEIKR | 24 |
| Heavy Chain Variable Region | AEVQLVESGGGVVRPGGSLRLSCAASG FTFDDYGMSWVRQAPGKGLEWVSGINW NGGSTGYADSVKGRFTISRDNAKNSLY LQMNSLRAEDTAVYYCARGVLSRYFDY WGQGTLVTVSS | 25 |

What is claimed:

1. An isolated antibody or antigen-binding portion thereof comprising the following heavy and light chain complimentarity determining regions (CDRs):
   a. a light chain CDR1 having the amino acid sequence of SEQ ID NO: 4;
   b. a light chain CDR2 having the amino acid sequence of SEQ ID NO: 5;
   c. a light chain CDR3 having the amino acid sequence of SEQ ID NO: 6;
   d. a heavy chain CDR1 having the amino acid sequence of SEQ ID NO: 1;
   e. a heavy chain CDR2 having the amino acid sequence of SEQ ID NO: 2; and
   f. a heavy chain CDR3 having the amino acid sequence of SEQ ID NO: 3.

2. The isolated antibody or antigen-binding portion thereof of claim 1, comprising the sequence of SEQ ID NO: 7, 24, or 25.

3. The isolated antibody or antigen-binding portion thereof of claim 2, further comprising a conservative substitution in a sequence not comprised by a CDR.

4. The isolated antibody or antigen-binding portion thereof of claim 1, wherein the antibody or polypeptide is selected from the group consisting of:
   an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody.

5. The isolated antibody or antigen-binding portion thereof of claim 1, wherein the isolated antibody or antigen-binding portion thereof is fully humanized.

6. The isolated antibody or antigen-binding portion thereof of claim 1, wherein the isolated antibody or antigen-binding portion thereof comprises fully humanized antigen-binding domains.

7. The isolated antibody or antigen-binding portion thereof of claim 1, wherein the isolated antibody or antigen-binding portion thereof specifically binds to CSPG4.

8. A pharmaceutical composition comprising an isolated antibody or antigen-binding portion thereof of claim 1 and a pharmaceutically acceptable carrier.

9. A nucleic acid encoding an isolated antibody or antigen-binding portion thereof of claim 1.

10. The nucleic acid of claim 9, wherein one or more of the nucleic acid sequences comprises a sequence selected from SEQ ID NOs: 8-11.

11. A cell comprising the nucleic acid of claim 9.

12. A composition comprising the isolated antibody or antigen-binding portion thereof of claim 1 and a chemotherapeutic agent.

13. A method of inhibiting or killing a CSPG4+ cell, the method comprising contacting the CSPG4+ cell with a composition of claim 12.

14. A method of treating cancer in a subject in need thereof, the method comprising administering a therapeutically effective amount of a composition of claim 12 to the subject.

15. The method of claim 14, wherein the cancer is selected from the group consisting of:
   melanoma; breast cancer; triple negative breast cancer; glioma; head and neck cancer; head and neck squamous cell carcinoma; carcinoma; mesothelioma; chordoma; condrosarcoma; sarcoma; leukemia; 11q23 positive acute leukemia; acute leukemia; and a CSPG4+ cancer or tumor.

* * * * *

SEQUENCE LISTING

<160> NUMBER OF SEQ ID NOS: 45

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Thr Phe Asp Asp Tyr Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Asn Trp Asn Gly Gly Ser Thr
1               5

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Arg Gly Val Leu Ser Arg Tyr Phe Asp Tyr
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Val Ser Ser Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 6

Gln Gln Arg Ser Asn Trp Pro Pro Ala
1               5

<210> SEQ ID NO 7
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala Glu Val Gln Leu Val Glu Ser Gly Gly Gly Val Val Arg Pro
1               5                   10                  15

Gly Gly Ser Leu Arg Leu Ser Cys Ala Ala Ser Gly Phe Thr Phe Asp
                20                  25                  30

Asp Tyr Gly Met Ser Trp Val Arg Gln Ala Pro Gly Lys Gly Leu Glu
            35                  40                  45

Trp Val Ser Gly Ile Asn Trp Asn Gly Ser Thr Gly Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Gly Val Leu Ser Arg Tyr Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Glu Leu Thr Gln Ser Pro Ala
130                 135                 140

Thr Leu Ser Leu Ser Pro Gly Glu Arg Ala Thr Leu Ser Cys Arg Ala
145                 150                 155                 160

Ser Gln Ser Val Ser Ser Tyr Leu Ala Trp Tyr Gln Gln Lys Pro Gly
                165                 170                 175

Gln Ala Pro Arg Leu Leu Ile Tyr Asp Ala Ser Asn Arg Ala Thr Gly
            180                 185                 190

Ile Pro Ala Arg Phe Ser Gly Ser Gly Ser Gly Thr Asp Phe Thr Leu
        195                 200                 205

Thr Ile Ser Ser Leu Glu Pro Glu Asp Phe Ala Val Tyr Tyr Cys Gln
    210                 215                 220

Gln Arg Ser Asn Trp Pro Pro Ala Phe Gly Gly Gly Thr Lys Val Glu
225                 230                 235                 240

Ile Lys Arg Ala Ala
            245

<210> SEQ ID NO 8
<211> LENGTH: 957
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
ttccggctcg tatgttgtgt ggaattgtga gcggataaca atttcacaca ggaaacagct      60

```
atgaccatga ttacgccaag cttgcatgca aattctattt caaggagaca gtcataatga      120
ataccctatt gcctacggca gccgctggat tgttattact cgcggcccag ccggccatgg      180
ccgaggtgca gctggtggag tctgggggag gtgtggtacg gcctgggggg tccctgagac      240
tctcctgtgc agcctctgga ttcacctttg atgattatgg catgagctgg gtccgccaag      300
ctccagggaa ggggctggag tgggtctctg gtattaattg gaatggtggt agcacaggtt      360
atgcagactc tgtgaagggc cgattcacca tctccagaga caacgccaag aactccctgt      420
atctgcaaat gaacagtctg agagccgagg acacggccgt gtattactgt gcaaggggcg      480
tgctgtcgcg ttattttgac tactgggccc aaggtaccct ggtcaccgtc tcgagtggtg      540
gaggcggttc aggcggaggt ggctctggcg gtggcggatc ggaaattgag ctcacacagt      600
ctccagccac cctgtctttg tctccagggg aaagagccac cctctcctgc agggccagtc      660
agagtgttag cagctactta gcctggtacc aacagaaacc tggccaggct cccaggctcc      720
tcatctatga tgcatccaac agggccactg gcatcccagc caggttcagt ggcagtgggt      780
ctgggacaga cttcactctc accatcagca gcctagagcc tgaagatttt gcagtttatt      840
actgtcagca gcgtagcaac tggcctccgg ctttcggcgg agggaccaag gtggagatca      900
aacgtgcggc cgcagaacaa aaactcatct cagaagagga tctgaatggg gccgcat       957

<210> SEQ ID NO 9
<211> LENGTH: 724
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
cgaggtgcag ctggtggagt ctgggggagg tgtggtacgg cctgggggt ccctgagact       60 ctcctgtgca gcctctggat tcacctttga tgattatggc atgagctggg tccgccaagc      120
tccagggaag gggctggagt gggtctctgg tattaattgg aatggtggta gcacaggtta      180
tgcagactct gtgaagggcc gattcaccat ctccagagac aacgccaaga actccctgta      240
tctgcaaatg aacagtctga gagccgagga cacggccgtg tattactgtg caaggggcgt      300
gctgtcgcgt tattttgact actggggcca aggtaccctg gtcaccgtct cgagtggtgg      360
aggcggttca ggcggaggtg gctctggcgg tggcggatcg gaaattgagc tcacacagtc      420
tccagccacc ctgtctttgt ctccagggga agagccacc ctctcctgca gggccagtca      480
gagtgttagc agctacttag cctggtacca acagaaacct ggccaggctc ccaggctcct      540
catctatgat gcatccaaca gggccactgg catcccagcc aggttcagtg gcagtgggtc      600
tgggacagac ttcactctca ccatcagcag cctagagcct gaagattttg cagtttatta      660
ctgtcagcag cgtagcaact ggcctccggc tttcggcgga gggaccaagg tggagatcaa      720
acgt                                                                  724

<210> SEQ ID NO 10
<211> LENGTH: 355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
cgaggtgcag ctggtggagt ctgggggagg tgtggtacgg cctgggggt ccctgagact       60
```

```
ctcctgtgca gcctctggat tcacctttga tgattatggc atgagctggg tccgccaagc    120
tccagggaag gggctggagt gggtctctgg tattaattgg aatggtggta gcacaggtta    180
tgcagactct gtgaagggcc gattcaccat ctccagagac aacgccaaga actccctgta    240
tctgcaaatg aacagtctga gaccgagga cacggccgtg tattactgtg caaggggcgt    300
gctgtcgcgt tattttgact actggggcca aggtaccctg gtcaccgtct cgagt         355
```

```
<210> SEQ ID NO 11
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gaaattgagc tcacacagtc tccagccacc ctgtctttgt ctccagggga aagagccacc    60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctccggc tttcggcgga    300
gggaccaagg tggagatcaa acgt                                           324
```

```
<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly Ser
1               5
```

```
<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 13

His His His His His His
1               5
```

```
<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30
```

```
Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Val Leu Ser Arg Tyr Phe Asp Tyr Trp Gly Gln Gly Thr
            100                 105                 110

Leu Val Thr Val Ser Ser
            115

<210> SEQ ID NO 15
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(354)

<400> SEQUENCE: 15 gag gtg cag ctg gtg gag tct ggg gga ggt gtg gta cgg cct ggg ggg     48
Glu Val Gln Leu Val Glu Ser Gly Gly Gly Val Val Arg Pro Gly Gly
 1               5                  10                  15 tcc ctg aga ctc tcc tgt gca gcc tct gga ttc acc ttt gat gat tat    96
Ser Leu Arg Leu Ser Cys Ala Ala Ser Gly Phe Thr Phe Asp Asp Tyr
            20                  25                  30 ggc atg agc tgg gtc cgc caa gct cca ggg aag ggg ctg gag tgg gtc   144
Gly Met Ser Trp Val Arg Gln Ala Pro Gly Lys Gly Leu Glu Trp Val
        35                  40                  45 tct ggt att aat tgg aat ggt ggt agc aca ggt tat gca gac tct gtg   192
Ser Gly Ile Asn Trp Asn Gly Gly Ser Thr Gly Tyr Ala Asp Ser Val
 50                  55                  60 aag ggc cga ttc acc atc tcc aga gac aac gcc aag aac tcc ctg tat   240
Lys Gly Arg Phe Thr Ile Ser Arg Asp Asn Ala Lys Asn Ser Leu Tyr
65                  70                  75                  80 ctg caa atg aac agt ctg aga gcc gag gac acg gcc gtg tat tac tgt   288
Leu Gln Met Asn Ser Leu Arg Ala Glu Asp Thr Ala Val Tyr Tyr Cys
                85                  90                  95 gca agg ggc gtg ctg tcg cgt tat ttt gac tac tgg ggc caa ggt acc   336
Ala Arg Gly Val Leu Ser Arg Tyr Phe Asp Tyr Trp Gly Gln Gly Thr
            100                 105                 110 ctg gtc acc gtc tcg agt                                            354
Leu Val Thr Val Ser Ser
            115

<210> SEQ ID NO 16
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Ile Glu Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
```

```
                  20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                 85                  90                  95

Ala Phe Gly Gly Gly Thr Lys Val Glu Ile Lys Arg Ala Ala
            100                 105                 110

<210> SEQ ID NO 17
<211> LENGTH: 332
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(330)

<400> SEQUENCE: 17 gaa att gag ctc aca cag tct cca gcc acc ctg tct ttg tct cca ggg     48
Glu Ile Glu Leu Thr Gln Ser Pro Ala Thr Leu Ser Leu Ser Pro Gly
1               5                   10                  15 gaa aga gcc acc ctc tcc tgc agg gcc agt cag agt gtt agc agc tac     96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc    144
Leu Ala Trp Tyr Gln Gln Lys Pro Gly Gln Ala Pro Arg Leu Leu Ile
         35                  40                  45 tat gat gca tcc aac agg gcc act ggc atc cca gcc agg ttc agt ggc    192
Tyr Asp Ala Ser Asn Arg Ala Thr Gly Ile Pro Ala Arg Phe Ser Gly
     50                  55                  60 agt ggg tct ggg aca gac ttc act ctc acc atc agc agc cta gag cct    240
Ser Gly Ser Gly Thr Asp Phe Thr Leu Thr Ile Ser Ser Leu Glu Pro
65                  70                  75                  80 gaa gat ttt gca gtt tat tac tgt cag cag cgt agc aac tgg cct ccg    288
Glu Asp Phe Ala Val Tyr Tyr Cys Gln Gln Arg Ser Asn Trp Pro Pro
                 85                  90                  95 gct ttc ggc gga ggg acc aag gtg gag atc aaa cgt gcg gcc gc         332
Ala Phe Gly Gly Gly Thr Lys Val Glu Ile Lys Arg Ala Ala
            100                 105                 110

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Phe Thr Phe Asp Asp Tyr Gly Met Ser
1               5                   10

<210> SEQ ID NO 19
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 19

Gly Ile Asn Trp Asn Gly Gly Ser Thr Gly Tyr Ala Asp Ser Val Lys
1               5                   10                  15

Gly

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Val Leu Ser Arg Tyr Phe Asp Tyr
1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ala Ser Gln Ser Val Ser Ser Tyr Leu Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Ala Ser Asn Arg Ala Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Gln Arg Ser Asn Trp Pro Pro Ala
1               5

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Ile Glu Leu Thr Gln Ser Pro Ala Thr Leu Ser Leu Ser Pro Gly
1               5                   10                  15
```

```
Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Ala Phe Gly Gly Gly Thr Lys Val Glu Ile Lys Arg
            100                 105
```

```
<210> SEQ ID NO 25
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Glu Val Gln Leu Val Glu Ser Gly Gly Gly Val Val Arg Pro Gly
 1               5                  10                  15

Gly Ser Leu Arg Leu Ser Cys Ala Ala Ser Gly Phe Thr Phe Asp Asp
                20                  25                  30

Tyr Gly Met Ser Trp Val Arg Gln Ala Pro Gly Lys Gly Leu Glu Trp
             35                  40                  45

Val Ser Gly Ile Asn Trp Asn Gly Gly Ser Thr Gly Tyr Ala Asp Ser
     50                  55                  60

Val Lys Gly Arg Phe Thr Ile Ser Arg Asp Asn Ala Lys Asn Ser Leu
 65                  70                  75                  80

Tyr Leu Gln Met Asn Ser Leu Arg Ala Glu Asp Thr Ala Val Tyr Tyr
                 85                  90                  95

Cys Ala Arg Gly Val Leu Ser Arg Tyr Phe Asp Tyr Trp Gly Gln Gly
            100                 105                 110

Thr Leu Val Thr Val Ser Ser
        115
```

```
<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Gly Gly Gly Ser
 1               5
```

```
<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27
```

```
Thr Gly Glu Lys Pro
1               5

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Arg Arg
1

<210> SEQ ID NO 29
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 1-5 "Gly Gly Gly
      Gly Ser" repeating units wherein some positions may be absent
<220> FEATURE:
<223> OTHER INFORMATION: See specification as filed for detailed
      description of substitutions and preferred embodiments

<400> SEQUENCE: 29

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Glu Gly Lys Ser Ser Gly Ser Gly Ser Glu Ser Lys Val Asp
1               5                   10

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Glu Ser Gly Ser Val Ser Ser Glu Gln Leu Ala Gln Phe Arg Ser
1               5                   10                  15

Leu Asp

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                           peptide

<400> SEQUENCE: 32

Gly Gly Arg Arg Gly Gly Gly Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Arg Gln Arg Asp Gly Glu Arg Pro
1               5

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Arg Gln Lys Asp Gly Gly Gly Ser Glu Arg Pro
1               5                   10

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Arg Gln Lys Asp Gly Gly Gly Ser Gly Gly Ser Glu Arg Pro
1               5                   10                  15

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Ser Thr Ser Gly Ser Gly Lys Pro Gly Ser Gly Glu Gly Ser Thr
1               5                   10                  15

Lys Gly

<210> SEQ ID NO 37
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-5 "Gly(1-5)-
      Ser(1-5)" repeating units wherein some positions may be absent
<220> FEATURE:
```

```
<223> OTHER INFORMATION: See specification as filed for detailed
      description of substitutions and preferred embodiments

<400> SEQUENCE: 37

Gly Gly Gly Gly Gly Ser Ser Ser Ser Gly Gly Gly Gly Gly Ser
1               5                   10                  15

Ser Ser Ser Ser Gly Gly Gly Gly Ser Ser Ser Ser Gly Gly
            20                  25                  30

Gly Gly Gly Ser Ser Ser Ser Gly Gly Gly Gly Ser Ser Ser
        35                  40                  45

Ser Ser
    50

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Glu Trp Ile Gly
1               5

<210> SEQ ID NO 39
<211> LENGTH: 296
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(294)

<400> SEQUENCE: 39 gag gtg cag ctg gtg gag tct ggg gga ggt gtg gta cgg cct ggg ggg        48
Glu Val Gln Leu Val Glu Ser Gly Gly Gly Val Val Arg Pro Gly Gly
1               5                   10                  15 tcc ctg aga ctc tcc tgt gca gcc tct gga ttc acc ttt gat gat tat       96
Ser Leu Arg Leu Ser Cys Ala Ala Ser Gly Phe Thr Phe Asp Asp Tyr
            20                  25                  30 ggc atg agc tgg gtc cgc caa gct cca ggg aag ggg ctg gag tgg gtc      144
Gly Met Ser Trp Val Arg Gln Ala Pro Gly Lys Gly Leu Glu Trp Val
        35                  40                  45 tct ggt att aat tgg aat ggt ggt agc aca ggt tat gca gac tct gtg      192
Ser Gly Ile Asn Trp Asn Gly Gly Ser Thr Gly Tyr Ala Asp Ser Val
    50                  55                  60 aag ggc cga ttc acc atc tcc aga gac aac gcc aag aac tcc ctg tat      240
Lys Gly Arg Phe Thr Ile Ser Arg Asp Asn Ala Lys Asn Ser Leu Tyr
65                  70                  75                  80 ctg caa atg aac agt ctg aga gcc gag gac acg gcc ttg tat cac tgt      288
Leu Gln Met Asn Ser Leu Arg Ala Glu Asp Thr Ala Leu Tyr His Cys
                85                  90                  95 gcg aga ga                                                            296
Ala Arg

<210> SEQ ID NO 40
<211> LENGTH: 98
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg

<210> SEQ ID NO 41
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala

<210> SEQ ID NO 42
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
```

```
                    50                   55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr His Cys
                    85                  90                  95

Ala Arg

<210> SEQ ID NO 43
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(285)

<400> SEQUENCE: 43 gaa att gtg ttg aca cag tct cca gcc acc ctg tct ttg tct cca ggg      48
Glu Ile Val Leu Thr Gln Ser Pro Ala Thr Leu Ser Leu Ser Pro Gly
 1               5                  10                  15 gaa aga gcc acc ctc tcc tgc agg gcc agt cag agt gtt agc agc tac      96
Glu Arg Ala Thr Leu Ser Cys Arg Ala Ser Gln Ser Val Ser Ser Tyr
                20                  25                  30 tta gcc tgg tac caa cag aaa cct ggc cag gct ccc agg ctc ctc atc     144
Leu Ala Trp Tyr Gln Gln Lys Pro Gly Gln Ala Pro Arg Leu Leu Ile
            35                  40                  45 tat gat gca tcc aac agg gcc act ggc atc cca gcc agg ttc agt ggc     192
Tyr Asp Ala Ser Asn Arg Ala Thr Gly Ile Pro Ala Arg Phe Ser Gly
        50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
 65                  70                  75                  80 gaa gat ttt gca gtt tat tac tgt cag cag cgt agc aac tgg cct cc      287
Glu Asp Phe Ala Val Tyr Tyr Cys Gln Gln Arg Ser Asn Trp Pro
                85                  90                  95

<210> SEQ ID NO 44
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro
                85                  90                  95

<210> SEQ ID NO 45
```

```
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Ile Glu Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95
```